US006974808B2

(12) United States Patent
McCarthy

(10) Patent No.: US 6,974,808 B2
(45) Date of Patent: Dec. 13, 2005

(54) CRF RECEPTOR ANTAGONISTS AND METHODS RELATING THERETO

(75) Inventor: James R. McCarthy, Zionsville, IN (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 09/995,159

(22) Filed: Nov. 27, 2001

(65) Prior Publication Data

US 2002/0049207 A1 Apr. 25, 2002

Related U.S. Application Data

(62) Division of application No. 09/415,503, filed on Oct. 8, 1999, now Pat. No. 6,352,990, which is a continuation of application No. PCT/US98/02932, filed on Feb. 17, 1998.

(51) Int. Cl.[7] .................... C07D 471/04; A61K 31/437; A61P 25/22; A61P 25/24
(52) U.S. Cl. ..................... 514/217.03; 514/217.03; 514/231.5; 514/303; 546/273.4; 544/111; 540/599
(58) Field of Search ..................... 546/272.7, 273.4; 514/303, 231.5, 217.03; 544/111; 540/599

(56) References Cited

U.S. PATENT DOCUMENTS

| 4,605,642 A | 8/1986 | Rivier et al. ........... 514/12 |
| 5,063,245 A | 11/1991 | Abreu et al. ........... 514/404 |
| 5,464,847 A | 11/1995 | Courtemanche et al. ... 514/342 |
| 6,352,990 B1 | 3/2002 | McCarthy ............ 514/261 |

FOREIGN PATENT DOCUMENTS

| AU | 41399/93 | 1/1994 |
| EP | 0 773 023 A1 | 5/1997 |
| EP | 0 778 277 A1 | 5/1997 |
| EP | 0 812 831 A1 | 12/1997 |
| WO | WO 94/13676 | 6/1994 |
| WO | WO 94/13677 | 6/1994 |
| WO | WO 95/33750 | 12/1995 |
| WO | WO 95/34563 | 12/1995 |
| WO | WO 96/35689 | 11/1996 |
| WO | WO 97/29109 | 8/1997 |
| WO | WO 98/03510 | 1/1998 |
| WO | WO 98/08846 | 3/1998 |
| WO | WO 98/08847 | 3/1998 |
| WO | WO 98/35967 | 8/1998 |

OTHER PUBLICATIONS

Mitchell, Neurosci. Neurosci. Biobehav. Rev. 22(5); 635–651, 1998.*
Kiyama et al. Chem. Pharm. Bull., 43(3) 450–460, 1995.*
Adamiak, et al., *Angew. Chem.*, 1985, 97/(12), 1046 (CA 104:110099, 1986).
Brown, et al., *J. Chem. Soc.*, 1969, C18, 2620–2624 (CA 72:21662, 1970).
Gundersen, et al., *Tetrahedron Letts.*, 1994, 50(32), 9743–9756.
Hamann, et al., *Can. J. Chem.*, 1968, 46(3), 419–423 (CA 68:68957, 1968).
*J. Heterocycl. Chem.*, 1968, 5(5), 679–682 (CA 70:4052, 1969).
McKenzie, et al., *J. Org. Chem.*, 1982, 47(25), 4881–4884.
Stevenson, et al., *Tetrahedron Letts.*, 1996, 37(46), 8375–8378.
Wang, et al., *Biochem. Pharmacol.*, 1979, 28(15), 2249–2260 (CA 92:69336, 1980).
Al–Shaar. A..H., et al., "The synthesis of heterocycles via addition–elimination reactions of 4– and 5–aminoimidazoles," *J. Chem. Soc., Perkin Trans. 1*, 1992, 2789–2793.
Balicki, R., et al., Translocative rearrangements. Generality of the formamidine–induced rearrangement of 4–substituted 5–amino–4–cyano–4H–imidazoles, *J. Org. Chem.*, 1983, 48(1), 3–7.
Battaglia, G., et al., "Characterization of corticotrophin–releasing factor receptor–mediated adenylate cyclase activity in the rat central nervous system," *Synapse, Alan R. Liss, Inc.* 1987, 1, 572–581.
Bilezikjian, L.M., et al., "Glucocorticoids inhibit Corticotrophin–releasing factor–induced production of adenosine 3',5'-monophosphate in cultured anterior pituitary cells," *Endocrinology*, 1983, 113(2), 657–662.
Boger, D.L., et al., "Inverse electron demand diels–alder reactions of heterocyclic aza dienes. Studies on the total synthesis of lavendamycin: investigative studies on the preparation of the CDE β–carboline ring system and AB quinoline–5,8–quinone ring system," *J. Org. Chem.*, 1985, 50(26), 5782–5789.
Borch, R.F., et al., "A new method for the methylation of amines," *J. Org. Chem.*, 1972, 37(10), 1673–1674.
Brown, M.R., et al., "Corticotropin–releasing factor: actions on the sympathetic nervous system and metabolism," *Endocrinology*, 1982, 111(3), 928–931.
Brown, et al., "Corticotropin–releasing factor: effects on the sympatheic nervous system and oxygen consumption," *Life Sciences*, 1982, 30, 207–210.
Chen, R., et al., "Expression cloning of a human corticotrophin–releasing–factor receptor," *PNAS, USA*, Oct. 1993, 90, 8967–8971.
Cheng, Y.–C., et al., "Relationship between the inhibition constant ($K_I$) and the concentration of inhibitor which causes 50 per cent inhibition ($I_{50}$) of an enzymatic reaction," *Biochem. Pharmacol.*, 1973, 22, 3099–3108.

(Continued)

*Primary Examiner*—Venkataraman Balasubramanian
(74) *Attorney, Agent, or Firm*—Shah R. Makujina; Woodcock Washburn, LLP

(57) ABSTRACT

CRF receptor antagonists are disclosed which have utility in the treatment of a variety of disorders, including the treatment of disorders manifesting hypersecretion of CRF in a warm-blooded animals, such as stroke.

5 Claims, No Drawings

OTHER PUBLICATIONS

Chatani, N., et al., "Palladium– and nickel–catalyzed reaction of trimethylsilyl cyanide with acetylenes. Addition of trimethysilyl cyanide to the carbon–carbon triple bonds," *J. Org. Chem.*, 1988, 53, 3539–3548.

Corey, E.J., et al., "A synthetic method for formyl→ethynyl conversion (RCHO →RC≡CH or RC≡CR')," *Tetrahderon Letts.*, 1972, 36, 3769–3772.

Crofford, L.J., et al., "Local secretion of corticotrophin–releasing hormone in the joints of lewis rats with inflammatory arthritis," *J. Clin. Invest.*, Dec. 1992, 90, 2555–2564.

DeSouza, E.B., "Role of corticotrophin–releasing factor in neuropsychiatric disorders and neurodegenerative diseases," *Ann. Reports in Med. Chem.*, 1990, 25, Chapter 23, 215–223.

DeSouza, E.B., et al., "Corticotropin–releasing factor receptors in the pituitary gland and central nervous system: methods and overview," *Methods Enzymol.*, 1986, 124, 560–590.

DeSouza, E.B., et al., "Corticotropin–releasing factor receptors in rat forebrain autoradiographic identification," *Science*, Jun. 1984, 224(4656, 1449–1451.

DeSouza, E.B., et al., "Corticotropin–releasing factor receptors in the rat central nervous system: characterization and regional distribution," *J. of Neuroscience*, Jan. 1987, 7(1), 88–100.

Ehlers, C.L., et al., "Corticotropin releasing factor produces increases in brain excitability and convulsive seizures in rats," *Brain Res.*, 1983, 278, 332–336.

Estel, L., et al., "Metalation/$S_{RN}1$ coupling in heterocyclic synthesis. A convenient methodology for ring functionalization," *J. Org. Chem.*, 1988, 53(12), 2740–2744.

Fisher, L.A., et al., "Corticotropin–releasing factor (CRF): Central effects on mean arerial pressure and heart rate in rats," *Endocrinology*, 1982, 110(6), p. 2222.

Houston, D.M., et al., "Potential Inhibitors of S–adenosyl-methionine–dependent methyltransferases. 8. Molecular dissections of carbocyclic 3–deazaadenosine as inhibitors of S–adenosylhomocysteine hydrolase," *J. Org. Chem.*, 1985, 28, 467–471.

Irwin, M., et al., "CRF activates autonomic nervous system and reduces natural killer cytotoxicity," *Am. J. Physiol.*, 1988, 255(5), R744–R747.

Klinge, D.E., et al., "Ring transformations in reactions of heterocyclic halogeno compounds with nucleophiles (XXXVI). Conversion of 4–amino–3–halogenopyridazines into pyrazoles and of 4–amino–3,6–dihalogenopyridazines into 1,2,4–triazoles," *J. of the Royal Netherlands Chem. Soc.*, Aug. 1974, 93(8), 236–239.

Kuraishi, T., et al., "The synthesis of imidazo [4,5–c]–, s–triazolo [4,3–b]–, and tetrazolo [1,5–b] pyridazines," *J. Heterocyclic Chem.*, Feb. 1964, 1(1), 42–47.

Levine, A.S., et al., "Effect of centrally administered corticotrophin releasing factor (CRF) on multiple feeding paradigms," *Neuropharmacology*, 1983, 22(3A), 337–339.

Munson, P.J., et al., "LIGAND: A versatile computerized approach for characterization of ligand–binding systems," *Anal. Biochem., Academic Press, Inc.* 1980, 107, 220–239.

Perrin, M.H., et al., "Corticotrophin–releasing factor binding to the anterior pituitary receptor is modulated by divalent cations and guanyl nucleotides," *Endocrinology*, 1986, 118(3), 1171–1179.

Perrin, M.H., et al., "Cloning and functional expression of a rat brain corticotrophin releasing factor (CRF) receptor," *Endo.*, 1993, 133(6), 3058–3061.

Remington's Pharmaceutical Science, Gennaro (Ed.), Mack Publishing Co., Easton, PA, 1990.

Rivier, J., et al., "Characterization of rat hypothalmic corticotrophin–releasing factor," *Proc. Natl. Acad. Sci. USA*, Aug. 1983, 80, 4851–4855.

Rivier, J., et al., "Synthetic competitive antagonists of corticotrophin–releasing factor: effect on ACTH secretion in the rat," *Science*, May 1984, 224(4651), 889–891.

Sapolsky, R., et al., "Interleukin–1 stimulates the secretion of hypothalamic corticotrophin–releasing fatcor," *Science*, Oct. 23, 1987, 238, 522–524.

Shibahara, S., et al., "Isolation and sequence analysis of the human corticotrophin–releasing factor precursor gene," *EMBO J.*, 1983, 2(5), 775–779.

Sirinathsinghji, D.J.S., et al., "Corticotropin–releasing factor is a potent inhibitor of sexual receptivity in the female rat," *Nature*, Sep. 15, 1983, 305, 232–235.

Sutton, R.E., et al., "Corticotrophin releasing factor produces behavioural activation in rats," *Nature*, May 27, 1982, 297, 331–333.

Tilders, F.J.H., et al., "Effect of hypothalamus lesions on the presence of CRF–immunoreactive nerve terminals in the median eminence and on the pituitary–adrenal response to stress," *Regul. Peptides*, 1982, 5, 77–84.

Udelsman, R., et al., "Functional corticotrophin releasing factor receptors in the primate peripheral sympathetic nervous system," *Nature*, Jan. 9, 1986, 319, 147–150.

Vale, W., et al., "Characterization of a 41–residue ovine hypothalamic peptide that stimulates secretion of corticotrophin and β–endorphin," *Science*, Sep. 1981, 213, 1394–1397.

Vita, N., et al., "Primary structure and functional expression of mouse pituitary and human brain corticotrophin releasing factor receptors," *FEBS*, NOv. 1993, 335(1), 1–5.

Webster, E.L., et al., "Corticotrophin–releasing factor receptors in mouse spleen: identification, autoradiographic localization, and regulation by divalent cations and guanine nucleotides," *Endocrinology*, 1988, 122(2), 609–617.

Williams, C.L., et al., "Corticotrophin–releasing factor directly mediates colonic responses to stress," *Am. J. Physiol.*, 1987, 253, G582–G586.

Wynn, P.C., et al., "Properties and regulation of high–affinity pituitary receptors for corticotrophin–releasing factor," *Biochem. & Biophys. Res. Comm.*, Jan. 27, 1983, 110(2), 602–608.

\* cited by examiner

CRF RECEPTOR ANTAGONISTS AND METHODS RELATING THERETO

CROSS REFERENCE

This application is a divisional application of Ser. No. 09/415,503, filed Oct. 8, 1999, now U.S. Pat. No. 6,352,990, which is a continuation of international application number PCT/US98/02932, filed Feb. 17, 1998.

TECHNICAL FIELD

This invention relates generally to CRF receptor antagonists, and to methods of treating disorders by administration of such antagonists to a warm-blooded animal in need thereof.

BACKGROUND OF THE INVENTION

The first corticotropin-releasing factor (CRF) was isolated from ovine hypothalmi and identified as a 41-amino acid peptide (Vale et al., *Science* 213:1394–1397, 1981). Subsequently, sequences of human and rat CRF were isolated and determined to be identical, but different from ovine CRF in 7 of the 41 amino acid residues (Rivier et al., *Proc. Natl. Acad. Sci. USA* 80:4851, 1983; Shibahara et al., *EMBO J.* 2:775, 1983).

CRF has been found to produce profound alterations in endocrine, nervous and immune system function. CRF is believed to be the major physiological regulator of the basal and stress-release of adrenocorticotropic hormone ("ACTH"), β-endorphin, and other pro-opiomelanocortin ("POMC")-derived peptides from the anterior pituitary (Vale et al., *Science* 213:1394–1397, 1981). Briefly, CRF is believed to initiate its biological effects by binding to a plasma membrane receptor which has been found to be distributed throughout the brain (DeSouza et al., *Science* 224:1449–1451, 1984), pituitary (DeSouza et al., *Methods Enzymol.* 124:560, 1986; Wynn et al., *Biochem. Biophys. Res. Comm.* 110:602–608, 1983), adrenals (Udelsman et al., *Nature* 319:147–150, 1986) and spleen (Webster, E. L., and E. B. DeSouza, *Endocrinology* 122:609–617, 1988). The CRF receptor is coupled to a GTP-binding protein (Perrin et al., *Endocrinology* 118:1171–1179, 1986) which mediates CRF-stimulated increase in intracellular production of cAMP (Bilezikjian, L. M., and W. W. Vale, *Endocrinology* 113:657–662, 1983). The receptor for CRF has now been cloned from rat (Perrin et al., *Endo* 133(6):3058–3061, 1993), and human brain (Chen et al., *PNAS* 90(19):8967–8971, 1993; Vita et al., *FEBS* 335(1):1–5, 1993). This receptor is a 415 amino acid protein comprising seven membrane spanning domains. A comparison of identity between rat and human sequences shows a high degree of homology (97%) at the amino acid level.

In addition to its role in stimulating the production of ACTH and POMC, CRF is also believed to coordinate many of the endocrine, autonomic, and behavioral responses to stress, and may be involved in the pathophysiology of affective disorders. Moreover, CRF is believed to be a key intermediary in communication between the immune, central nervous, endocrine and cardiovascular systems (Crofford et al., *J. Clin. Invest.* 90:2555–2564, 1992; Sapolsky et al., *Science* 238:522–524, 1987; Tilders et al., *Regul. Peptides* 5:77–84, 1982). Overall, CRF appears to be one of the pivotal central nervous system neurotransmitters and plays a crucial role in integrating the body's overall response to stress.

Administration of CRF directly to the brain elicits behavioral, physiological, and endocrine responses identical to those observed for an animal exposed to a stressful environment. For example, intracerebroventricular injection of CRF results in behavioral activation (Sutton et al., *Nature* 297:331, 1982), persistent activation of the electroencephalogram (Ehlers et al., *Brain Res.* 278:332, 1983), stimulation of the sympathoadrenomedullary pathway (Brown et al., *Endocrinology* 110:928, 1982), an increase of heart rate and blood pressure (Fisher et al., *Endocrinology* 110:2222, 1982), an increase in oxygen consumption (Brown et al., *Life Sciences* 30:207, 1982), alteration of gastrointestinal activity (Williams et al., *Am. J. Physiol.* 253:G582, 1987), suppression of food consumption (Levine et al., *Neuropharmacology* 22:337, 1983), modification of sexual behavior (Sirinathsinghji et al., *Nature* 305:232, 1983), and immune function compromise (Irwin et al., *Am. J. Physiol.* 255:R744, 1988). Furthermore, clinical data suggests that CRF may be hypersecreted in the brain in depression, anxiety-related disorders, and anorexia nervosa. (DeSouza, *Ann. Reports in Med. Chem.* 25:215–223, 1990). Accordingly, clinical data suggests that CRF receptor antagonists may represent novel antidepressant and/or anxiolytic drugs that may be useful in the treatment of the neuropsychiatric disorders manifesting hypersecretion of CRF.

The first CRF receptor antagonists were peptides (see, e.g., Rivier et al., U.S. Pat. No. 4,605,642; Rivier et al., *Science* 224:889, 1984). While these peptides established that CRF receptor antagonists can attenuate the pharmacological responses to CRF, peptide CRF receptor antagonists suffer from the usual drawbacks of peptide therapeutics including lack of stability and limited oral activity. More recently, small molecule CRF receptor antagonists have been reported. For example, substituted 4-thio-5-oxo-3-pyyrazoline derivatives (Abreu et al., U.S. Pat. No. 5,063, 245) and substituted 2-aminothiazole derivatives (Courtemanche et al., Australian Patent No. AU-A-41399/93) have been reported as CRF receptor antagonists. These particular derivatives were found to be effective in inhibiting the binding of CRF to its receptor in the 1–10 $\mu$M range and 0.1–10 $\mu$M range, respectively.

Due to the physiological significance of CRF, the development of biologically-active small molecules having significant CRF receptor binding activity and which are capable of antagonizing the CRF receptor remains a desirable goal. Such CRF receptor antagonists would be useful in the treatment of endocrine, psychiatric and neurologic conditions or illnesses, including stress-related disorders in general.

While significant strides have been made toward achieving CRF regulation through administration of CRF receptor antagonists, there remains a need in the art for effective small molecule CRF receptor antagonists. There is also a need for pharmaceutical compositions containing such CRF receptor antagonists, as well as methods relating to the use thereof to treat, for example, stress-related disorders. The present invention fulfills these needs, and provides other related advantages.

SUMMARY OF THE INVENTION

In brief, this invention is generally directed to CRF receptor antagonists, and more specifically to CRF receptor antagonists having the following general structures (I) through (VI):

(I)

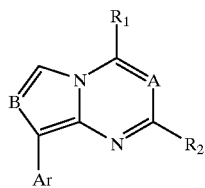

(II)

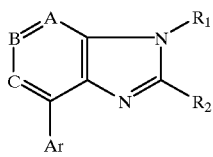

(III)

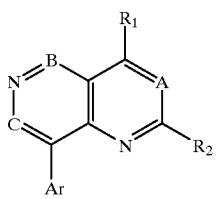

(IV)

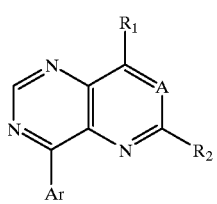

(V)

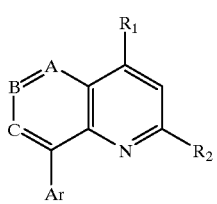

(VI)

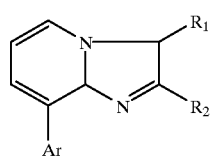

where A, B, C, Ar, $R_1$, and $R_2$, are as identified in the following detailed description.

The CRF receptor antagonists of this invention have utility over a wide range of therapeutic applications, and may be used to treat a variety of disorders or illnesses, including stress-related disorders. Such methods include administering an effective amount of a CRF receptor antagonist of this invention, preferably in the form of a pharmaceutical composition, to an animal in need thereof. Accordingly, in another embodiment, pharmaceutical compositions are disclosed containing one or more CRF receptor antagonists of this invention in combination with a pharmaceutically acceptable carrier and/or diluent.

These and other aspects of the invention will be apparent upon reference to the following detailed description. To this end, various references are set forth herein which describe in more detail certain procedures, compounds and/or compositions, and are hereby incorporated by reference in their entirety.

DETAILED DESCRIPTION OF THE INVENTION

The present invention is directed generally to compounds useful as corticotropin-releasing factor (CRF) receptor antagonists.

In a first embodiment, the CRF receptor antagonists of this invention have the following structure (I):

(I)

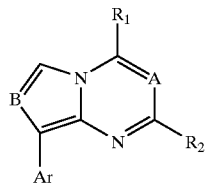

including stereoisomers and pharmaceutically acceptable salts thereof, wherein:

A and B are selected from CR and N;
R is selected from hydrogen and $C_{1-6}$alkyl;
$R_1$ is $NR_3R_4$;
$R_2$ is $C_{1-6}$alkyl;
$R_3$ is selected from hydrogen, $C_{1-6}$alkyl, mono- or di($C_{3-6}$cycloalkyl)methyl, $C_{3-6}$cycloalkyl, $C_{3-6}$alkenyl; hydroxy $C_{1-6}$alkyl, $C_{1-6}$alkylcarbonyloxy$C_{1-6}$alkyl and $C_{1-6}$alkyloxy$C_{1-6}$alkyl;
$R_4$ is selected from $C_{1-8}$alkyl, mono- or di($C_{3-6}$cycloalkyl)methyl, $Ar^1CH_2$, $C_{3-6}$alkenyl, $C_{1-6}$alkyloxy$C_{1-6}$alkyl, hydroxy$C_{1-6}$alkyl, thienylmethyl, furanylmethyl, $C_{1-6}$alkylthio$C_{1-6}$alkyl, morpholinyl, mono- or di($C_{1-6}$alkyl)amino$C_{1-6}$alkyl, di($C_{1-6}$alkyl)amino, $C_{1-6}$alkylcarbonyl$C_{1-6}$alkyl, $C_{1-6}$alkyl substituted with imidazolyl; or a radical of the formula —($C_{1-6}$alkanediyl)-O—CO—$Ar^1$;
or $R_3$ and $R_4$ taken together with the nitrogen atom to which they are attached form a pyrrolidinyl, piperidinyl, homopiperidinyl or morpholinyl group, optionally substituted with $C_{1-6}$alkyl or $C_{1-6}$alkyloxy;
Ar is selected from phenyl substituted with 1, 2 or 3 substituents independently selected from halo, $C_{1-6}$alkyl, triflouromethyl, cyano, $C_{1-6}$alkyloxy, benzyloxy, $C_{1-6}$alkylthio, nitro, amino and mono- and di($C_{1-6}$alkyl)amino; and pyridinyl substituted with 1, 2 or 3 substituents independently selected from halo, $C_{1-6}$alkyl, triflouromethyl, hydroxy, cyano, $C_{1-6}$alkyloxy, benzyloxy, $C_{1-6}$alkylthio, nitro, amino, mono- and di($C_{1-6}$alkyl)amino and piperidinyl; and
$Ar^1$ is selected from phenyl, pyridinyl, and phenyl substituted with 1, 2 or 3 substituents independently selected from halo, $C_{1-6}$alkyl, $C_{1-6}$alkyloxy, di($C_{1-6}$alkyl)amino$C_{1-6}$alkyl, triflouromethyl and $C_{1-6}$alkyl substituted with morpholinyl.

According, the CRF receptor antagonists of this embodiment have one of the following structures (Ia), (Ib), (Ic) and (Id):

(Ia)

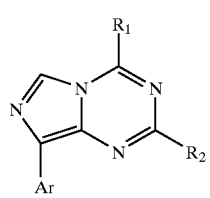

-continued (Ib)

(Ic)

(Id)

In a second embodiment, the CRF receptor antagonists of this invention have the following structure (II):

(II)

including stereoisomers and pharmaceutically acceptable salts thereof, wherein:

A, B and C are selected from CR and N, with the proviso that when B is N both A and C are CR;

R is selected from hydrogen and $C_{1-6}$alkyl;

$R_1$ is selected from $NR_3R_4$ and $R_5$;

$R_2$ is $C_{1-6}$alkyl;

$R_3$ is selected from hydrogen, $C_{1-6}$alkyl, mono- or di($C_{3-6}$cycloalkyl)methyl, $C_{3-6}$cycloalkyl; $C_{3-6}$alkenyl; hydroxy $C_{1-6}$alkyl, $C_{1-6}$alkylcarbonyloxy$C_{1-6}$alkyl and $C_{1-6}$alkyloxy$C_{1-6}$alkyl;

$R_4$ and $R_5$ are independently selected from $C_{1-8}$alkyl, mono- or di($C_{3-6}$cycloalkyl)methyl, $Ar^1CH_2$, $C_{3-6}$alkenyl, $C_{1-6}$alkyloxy$C_{1-6}$alkyl, hydroxy$C_{1-6}$alkyl, thienylmethyl, furanylmethyl, $C_{1-6}$alkylthio$C_{1-6}$alkyl, morpholinyl, mono- or di($C_{1-6}$alkyl)amino$C_{1-6}$alkyl, di($C_{1-6}$alkyl)amino, $C_{1-6}$alkylcarbonyl$C_{1-6}$alkyl, $C_{1-6}$alkyl substituted with imidazolyl; or a radical of the formula —($C_{1-6}$alkanediyl)-O—CO—$Ar^1$;

or $R_3$ and $R_4$ taken together with the nitrogen atom to which they are attached form a pyrrolidinyl, piperidinyl, homopiperidinyl or morpholinyl group, optionally substituted with $C_{1-6}$alkyl or $C_{1-6}$alkyloxy;

Ar is selected from phenyl substituted with 1, 2 or 3 substituents independently selected from halo, $C_{1-6}$alkyl, triflouromethyl, cyano, $C_{1-6}$alkyloxy, benzyloxy, $C_{1-6}$alkylthio, nitro, amino and mono- and di($C_{1-6}$alkyl)amino; and pyridinyl substituted with 1, 2 or 3 substituents independently selected from halo, $C_{1-6}$alkyl, triflouromethyl, hydroxy, cyano, $C_{1-6}$alkyloxy, benzyloxy, $C_{1-6}$alkylthio, nitro, amino, mono- and di($C_{1-6}$alkyl)amino and piperidinyl; and $Ar^1$ is selected from phenyl, pyridinyl, and phenyl substituted with 1, 2 or 3 substituents independently selected from halo, $C_{1-6}$alkyl, $C_{1-6}$alkyloxy, di($C_{1-6}$alkyl)amino$C_{1-6}$alkyl, triflouromethyl and $C_{1-6}$alkyl substituted with morpholinyl.

According, the CRF receptor antagonists of this embodiment have one of the following structures (IIa), (IIb), (IIc), (IId) and (IIe):

(IIa)

(IIb)

(IIc)

(IId)

(IIe)

In a third embodiment, the CRF receptor antagonists of this invention have the following structure (III):

(III)

including stereoisomers and pharmaceutically acceptable salts thereof, wherein:

A, B and C are selected from CR and N, with the proviso that one, and only one, of B and C is N;

R is selected from hydrogen and $C_{1-6}$alkyl;

$R_1$ is $NR_3R_4$;

$R_2$ is $C_{1-6}$alkyl;

$R_3$ is selected from hydrogen, $C_{1-6}$alkyl, mono- or di($C_{3-6}$cycloalkyl)methyl, $C_{3-6}$cycloalkyl; $C_{3-6}$alkenyl; hydroxy $C_{1-6}$alkyl, $C_{1-6}$alkylcarbonyloxy$C_{1-6}$alkyl and $C_{1-6}$alkyloxy$C_{1-6}$alkyl;

$R_4$ is selected from $C_{1-8}$alkyl, mono- or di($C_{3-6}$cycloalkyl) methyl, $Ar^1CH_2$, $C_{3-6}$alkenyl, $C_{1-6}$alkyloxy$C_{1-6}$alkyl, hydroxyC$_{1-6}$alkyl, thienylmethyl, furanylmethyl, C$_{1-6}$alkylthioC$_{1-6}$alkyl, morpholinyl, mono- or di(C$_{1-6}$alkyl)aminoC$_{1-6}$alkyl, di(C$_{1-6}$alkyl)amino, C$_{1-6}$alkylcarbonylC$_{1-6}$alkyl, C$_{1-6}$alkyl substituted with imidazolyl; or a radical of the formula —(C$_{1-6}$alkanediyl)-O—CO—Ar$^1$;

or R$_3$ and R$_4$ taken together with the nitrogen atom to which they are attached form a pyrrolidinyl, piperidinyl, homopiperidinyl or morpholinyl group, optionally substituted with C$_{1-6}$alkyl or C$_{1-6}$alkyloxy;

Ar is selected from phenyl substituted with 1, 2 or 3 substituents independently selected from halo, C$_{1-6}$alkyl, triflouromethyl, cyano, C$_{1-6}$alkyloxy, benzyloxy, C$_{1-6}$alkylthio, nitro, amino and mono- and di(C$_{1-6}$alkyl)amino; and pyridinyl substituted with 1, 2 or 3 substituents independently selected from halo, C$_{1-6}$alkyl, triflouromethyl, hydroxy, cyano, C$_{1-6}$alkyloxy, benzyloxy, C$_{1-6}$alkylthio, nitro, amino, mono- and di(C$_{1-6}$alkyl)amino and piperidinyl; and Ar$^1$ is selected from phenyl, pyridinyl, and phenyl substituted with 1, 2 or 3 substituents independently selected from halo, C$_{1-6}$alkyl, C$_{1-6}$alkyloxy, di(C$_{1-6}$alkyl)aminoC$_{1-6}$alkyl, triflouromethyl and C$_{1-6}$alkyl substituted with morpholinyl.

According, the CRF receptor antagonists of this embodiment have one of the following structures (IIIa) and (IIIb):

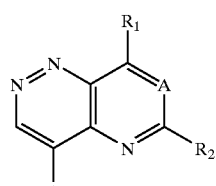

(IIIa)

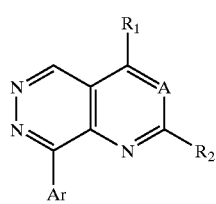

(IIIb)

In a fourth embodiment, the CRF receptor antagonists of this invention have the following structure (IV):

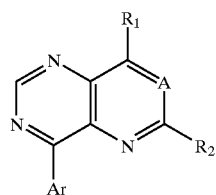

(IV)

including stereoisomers and pharmaceutically acceptable salts thereof, wherein:

A is selected from CR and N;
R is selected from hydrogen and C$_{1-6}$alkyl;
R$_1$ is NR$_3$R$_4$;
R$_2$ is C$_{1-6}$alkyl;
R$_3$ is selected from hydrogen, C$_{1-6}$alkyl, mono- or di(C$_{3-6}$cycloalkyl)methyl, C$_{3-6}$cycloalkyl; C$_{3-6}$alkenyl; hydroxy C$_{1-6}$alkyl, C$_{1-6}$alkylcarbonyloxyC$_{1-6}$alkyl and C$_{1-6}$alkyloxyC$_{1-6}$alkyl;
R$_4$ is selected from C$_{1-8}$alkyl, mono- or di(C$_{3-6}$cycloalkyl)methyl, Ar$^1$CH$_2$, C$_{3-6}$alkenyl, C$_{1-6}$alkyloxyC$_{1-6}$alkyl, hydroxyC$_{1-6}$alkyl, thienylmethyl, furanylmethyl, C$_{1-6}$alkylthioC$_{1-6}$alkyl, morpholinyl, mono- or di(C$_{1-6}$alkyl)aminoC$_{1-6}$alkyl, di(C$_{1-6}$alkyl)amino, C$_{1-6}$alkylcarbonylC$_{1-6}$alkyl, C$_{1-6}$alkyl substituted with imidazolyl; or a radical of the formula —(C$_{1-6}$alkanediyl)-O—CO—Ar$^1$;

or R$_3$ and R$_4$ taken together with the nitrogen atom to which they are attached form a pyrrolidinyl, piperidinyl, homopiperidinyl or morpholinyl group, optionally substituted with C$_{1-6}$alkyl or C$_{1-6}$alkyloxy;

Ar is selected from phenyl substituted with 1, 2 or 3 substituents independently selected from halo, C$_{1-6}$alkyl, triflouromethyl, cyano, C$_{1-6}$alkyloxy, benzyloxy, C$_{1-6}$alkylthio, nitro, amino and mono- and di(C$_{1-6}$alkyl)amino; and pyridinyl substituted with 1, 2 or 3 substituents independently selected from halo, C$_{1-6}$alkyl, triflouromethyl, hydroxy, cyano, C$_{1-6}$alkyloxy, benzyloxy, C$_{1-6}$alkylthio, nitro, amino, mono- and di(C$_{1-6}$alkyl)amino and piperidinyl; and Ar$^1$ is selected from phenyl, pyridinyl, and phenyl substituted with 1, 2 or 3 substituents independently selected from halo, C$_{1-6}$alkyl, C$_{1-6}$alkyloxy, di(C$_{1-6}$alkyl)aminoC$_{1-6}$alkyl, triflouromethyl and C$_{1-6}$alkyl substituted with morpholinyl.

According, the CRF receptor antagonists of the this embodiment have one of the following structures (IVa) and (IVb):

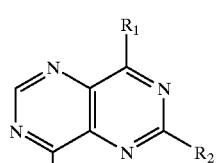

(IVa)

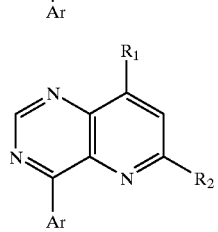

(IVb)

In a fifth embodiment, the CRF receptor antagonists of this invention have the following structure (V):

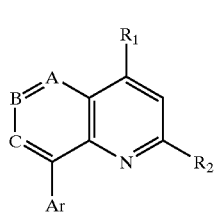

(V)

including stereoisomers and pharmaceutically acceptable salts thereof, wherein:

A, B and C are selected from CR and N, with the proviso that one, and only one, of A, B and C is N;
R is selected from hydrogen and C$_{1-6}$alkyl;
R$_1$ is NR$_3$R$_4$;
R$_2$ is C$_{1-6}$alkyl;
R$_3$ is selected from hydrogen, C$_{1-6}$alkyl, mono- or di(C$_{3-6}$cycloalkyl)methyl, C$_{3-6}$cycloalkyl; C$_{3-6}$alkenyl; hydroxy C$_{1-6}$alkyl, C$_{1-6}$alkylcarbonyloxyC$_{1-6}$alkyl and C$_{1-6}$alkyloxyC$_{1-6}$alkyl;

R$_4$ is selected from C$_{1-8}$alkyl, mono- or di(C$_{3-6}$cycloalkyl)methyl, Ar$^1$CH$_2$, C$_{3-6}$alkenyl, C$_{1-6}$alkyloxyC$_{1-6}$alkyl, hydroxyC$_{1-6}$alkyl, thienylmethyl, furanylmethyl, C$_{1-6}$alkylthioC$_{1-6}$alkyl, morpholinyl, mono- or di(C$_{1-6}$alkyl)aminoC$_{1-6}$alkyl, di(C$_{1-6}$alkyl)amino, C$_{1-6}$alkylcarbonylC$_{1-6}$alkyl, C$_{1-6}$alkyl substituted with imidazolyl; or a radical of the formula —(C$_{1-6}$alkanediyl)-O—CO—Ar$^1$;

or R$_3$ and R$_4$ taken together with the nitrogen atom to which they are attached form a pyrrolidinyl, piperidinyl, homopiperidinyl or morpholinyl group, optionally substituted with C$_{1-6}$alkyl or C$_{1-6}$alkyloxy;

Ar is selected from phenyl substituted with 1, 2 or 3 substituents independently selected from halo, C$_{1-6}$alkyl, triflouromethyl, cyano, C$_{1-6}$alkyloxy, benzyloxy, C$_{1-6}$alkylthio, nitro, amino and mono- and di(C$_{1-6}$alkyl)amino; and pyridinyl substituted with 1, 2 or 3 substituents independently selected from halo, C$_{1-6}$alkyl. triflouromethyl, hydroxy, cyano, C$_{1-6}$alkyloxy, benzyloxy, C$_{1-6}$alkylthio, nitro, amino, mono- and di(C$_{1-6}$alkyl)amino and piperidinyl; and Ar$^1$ is selected from phenyl, pyridinyl, and phenyl substituted with 1, 2 or 3 substituents independently selected from halo, C$_{1-6}$alkyl, C$_{1-6}$alkyloxy, di(C$_{1-6}$alkyl)aminoC$_{1-6}$alkyl, triflouromethyl and C$_{1-6}$alkyl substituted with morpholinyl.

According, the CRF receptor antagonists of this embodiment have one of the following structures (Va), (Vb) and (Vc):

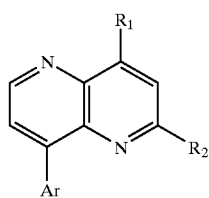
(Va)

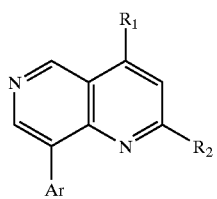
(Vb)

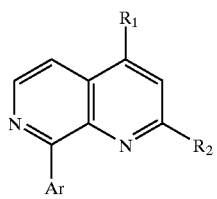
(Vc)

In a sixth embodiment, the CRF receptor antagonists of this invention have the following structure (VI):

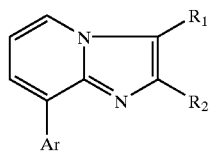
(VI)

including stereoisomers and pharmaceutically acceptable salts thereof, wherein:

R$_1$ is selected from NR$_3$R$_4$ and R$_5$;

R$_2$ is C$_{1-6}$alkyl;

R$_3$ is selected from hydrogen, C$_{1-6}$alkyl, mono- or di(C$_{3-6}$cycloalkyl)methyl, C$_{3-6}$cycloalkyl; C$_{3-6}$alkenyl; hydroxy C$_{1-6}$alkyl, C$_{1-6}$alkylcarbonyloxyC$_{1-6}$alkyl and C$_{1-6}$alkyloxyC$_{1-6}$alkyl;

R$_4$ and R$_5$ are independently selected from C$_{1-8}$alkyl, mono- or di(C$_{3-6}$cycloalkyl)methyl, Ar$^1$CH$_2$, C$_{3-6}$alkenyl, C$_{1-6}$alkyloxyC$_{1-6}$alkyl, hydroxyC$_{1-6}$alkyl, thienylmethyl, furanylmethyl, C$_{1-6}$alkylthioC$_{1-6}$alkyl, morpholinyl, mono- or di(C$_{1-6}$alkyl)aminoC$_{1-6}$alkyl, di(C$_{1-6}$alkyl)amino, C$_{1-6}$alkylcarbonylC$_{1-6}$alkyl, C$_{1-6}$alkyl substituted with imidazolyl; or a radical of the formula —(C$_{1-6}$alkanediyl)-O—CO—Ar$^1$;

or R$_3$ and R$_4$ taken together with the nitrogen atom to which they are attached form a pyrrolidinyl, piperidinyl, homopiperidinyl or morpholinyl group, optionally substituted with C$_{1-6}$alkyl or C$_{1-6}$alkyloxy;

Ar is selected from phenyl substituted with 1, 2 or 3 substituents independently selected from halo, C$_{1-6}$alkyl, triflouromethyl, cyano, C$_{1-6}$alkyloxy, benzyloxy, C$_{1-6}$alkylthio, nitro, amino and mono- and di(C$_{1-6}$alkyl)amino; and pyridinyl substituted with 1, 2 or 3 substituents independently selected from halo, C$_{1-6}$alkyl, triflouromethyl, hydroxy, cyano, C$_{1-6}$alkyloxy, benzyloxy, C$_{1-6}$alkylthio, nitro, amino, mono- and di(C$_{1-6}$alkyl)amino and piperidinyl; and Ar$^1$ is selected from phenyl, pyridinyl, and phenyl substituted with 1, 2 or 3 substituents independently selected from halo, C$_{1-6}$alkyl, C$_{1-6}$alkyloxy, di(C$_{1-6}$alkyl)aminoC$_{1-6}$alkyl, triflouromethyl and C$_{1-6}$alkyl substituted with morpholinyl.

The compounds of the present invention may be prepared by known organic synthesis techniques, including the methods described in more detail in the Examples.

The compounds of the present invention may generally be utilized as the free base. Alternatively, the compounds of this invention may be used in the form of acid addition salts. Acid addition salts of the free base amino compounds of the present invention may be prepared by methods well known in the art, and may be formed from organic and inorganic acids. Suitable organic acids include maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids.

The effectiveness of a compound as a CRF receptor antagonist may be determined by various assay methods. Suitable CRF antagonists of this invention are capable of inhibiting the specific binding of CRF to its receptor and antagonizing activities associated with CRF. A compound of structure (I) through (VI) may be assessed for activity as a CRF antagonist by one or more generally accepted assays for this purpose, including (but not limited to) the assays disclosed by DeSouza et al. (*J. Neuroscience* 7:88, 1987) and Battaglia et al. (*Synapse* 1:572, 1987). As mentioned above, suitable CRF antagonists include compounds which demonstrate CRF receptor affinity. CRF receptor affinity may be determined by binding studies that measure the ability of a compound to inhibit the binding of a radiolabeled CRF (e.g., [$^{125}$I]tyrosine-CFR) to its receptor (e.g., receptors prepared from rat cerebral cortex membranes). The radioligand binding assay described by DeSouza et al. (supra, 1987) provides an assay for determining a compound's affinity for the CRF receptor. Such activity is typically calculated from the $IC_{50}$ as the concentration of a compound necessary to displace 50% of the radiolabeled ligand from the receptor, and is reported as a "$K_i$" value calculated by the following equation:

$$K_i = \frac{IC_{50}}{1 + L/K_D}$$

where L=radioligand and $K_D$=affinity of radioligand for receptor (Cheng and Prusoff, *Biochem. Pharmacol.* 22:3099, 1973).

In addition to inhibiting CRF receptor binding, a compound's CRF receptor antagonist activity may be established by the ability of the compound to antagonize an activity associated with CRF. For example, CRF is known to stimulate various biochemical processes, including adenylate cyclase activity. Therefore, compounds may be evaluated as CRF antagonists by their ability to antagonize CRF-stimulated adenylate cyclase activity by, for example, measuring cAMP levels. The CRF-stimulated adenylate cyclase activity assay described by Battaglia et al. (supra, 1987) provides an assay for determining a compound's ability to antagonize CRF activity. Accordingly, CRF receptor antagonist activity may be determined by assay techniques which generally include an initial binding assay (such as disclosed by DeSouza (supra, 1987)) followed by a cAMP screening protocol (such as disclosed by Battaglia (supra, 1987)).

With reference to CRF receptor binding affinities, CRF receptor antagonists of this invention have a $K_i$ of less than 10 µM. In a preferred embodiment of this invention, a CRF receptor antagonist has a $K_i$ of less than 1 µM, and more preferably less than 0.25 µM (i.e., 250 nM).

The CRF receptor antagonists of the present invention demonstrate activity at the CRF receptor site, and may be used as therapeutic agents for the treatment of a wide range of disorders or illnesses including endocrine, psychiatric, and neurologic disorders or illnesses. More specifically, the CRF receptor antagonists of the present invention may be useful in treating physiological conditions or disorders arising from the hypersecretion of CRF. Because CRF is believed to be a pivotal neurotransmitter that activates and coordinates the endocrine, behavioral and automatic responses to stress, the CRF receptor antagonists of the present invention can be used to treat neuropsychiatric disorders. Neuropsychiatric disorders which may be treatable by the CRF receptor antagonists of this invention include affective disorders such as depression; anxiety-related disorders such as generalized anxiety disorder, panic disorder, obsessive-compulsive disorder, abnormal aggression, cardiovascular abnormalities such as unstable angina and reactive hypertension; and feeding disorders such as anorexia nervosa, bulimia, and irritable bowel syndrome. CRF antagonists may also be useful in treating stress-induced immune suppression associated with various diseases states, as well as stroke. Other uses of the CRF antagonists of this invention include treatment of inflammatory conditions (such as rheumatoid arthritis, uveitis, asthma, inflammatory bowel disease and G.I. motility), Cushing's disease, infantile spasms, epilepsy and other seizures in both infants and adults, and various substance abuse and withdrawal (including alcoholism).

In another embodiment of the invention, pharmaceutical compositions containing one or more CRF receptor antagonists are disclosed. For the purposes of administration, the compounds of the present invention may be formulated as pharmaceutical compositions. Pharmaceutical compositions of the present invention comprise a CRF receptor antagonist of the present invention (i.e., a compound of structure (I) through (VI)) and a pharmaceutically acceptable carrier and/or diluent. The CRF receptor antagonist is present in the composition in an amount which is effective to treat a particular disorder—that is, in an amount sufficient to achieve CRF receptor antagonist activity, and preferably with acceptable toxicity to the patient. Preferably, the pharmaceutical compositions of the present invention may include a CRF receptor antagonist in an amount from 0.1 mg to 250 mg per dosage depending upon the route of administration, and more preferably from 1 mg to 60 mg. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a CRF receptor antagonist, diluents, dispersing and surface active agents, binders, and lubricants. One skilled in this art may further formulate the CRF receptor antagonist in an appropriate manner, and in accordance with accepted practices, such as those disclosed in *Remington's Pharmaceutical Sciences*, Gennaro, Ed., Mack Publishing Co., Easton, Pa. 1990.

In another embodiment, the present invention provides a method for treating a variety of disorders or illnesses, including endocrine, psychiatric and neurologic disorders or illnesses. Such methods include administering of a compound of the present invention to a warm-blooded animal in an amount sufficient to treat the disorder or illness. Such methods include systemic administration of a CRF receptor antagonist of this invention, preferably in the form of a pharmaceutical composition. As used herein, systemic administration includes oral and parenteral methods of administration. For oral administration, suitable pharmaceutical compositions of CRF receptor antagonists include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds of the present invention can be prepared in aqueous injection solutions which may contain, in addition to the CRF receptor antagonist, buffers, antioxidants, bacteriostats, and other additives commonly employed in such solutions.

As mentioned above, administration of a compound of the present invention can be used to treat a wide variety of disorders or illnesses. In particular, the compounds of the present invention may be administered to a warm-blooded animal for the treatment of depression, anxiety disorder, panic disorder, obsessive-compulsive disorder, abnormal aggression, unstable angina, reactive hypertension, anorexia nervosa, bulimia, irritable bowel syndrome, stress-induced immune suppression, stroke, inflammation, Cushing's disease, infantile spasms, epilepsy, and substance abuse or withdrawal.

The following examples are provided for purposes of illustration, not limitation.

EXAMPLES

The CRF receptor antagonists of this invention may be prepared by the methods disclosed in Examples 1–19. Example 20 presents a method for determining the receptor

Example 1

Synthesis of Representative Compounds of Structure (I)

Part A, Pyrrolo[1,2-a]pyrimidines

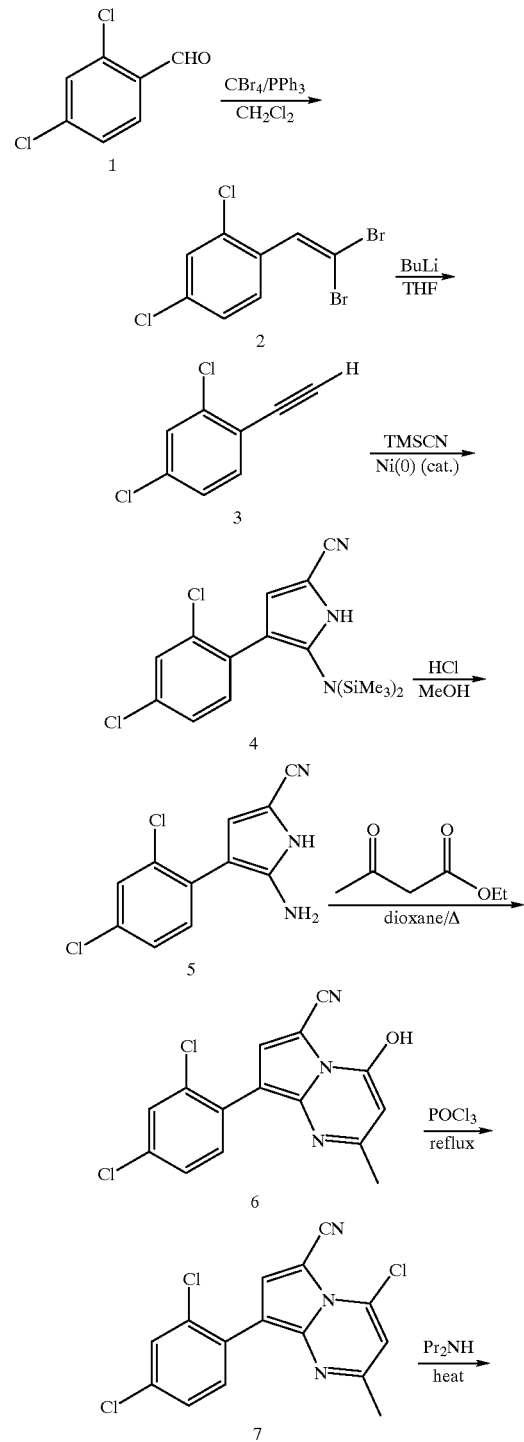

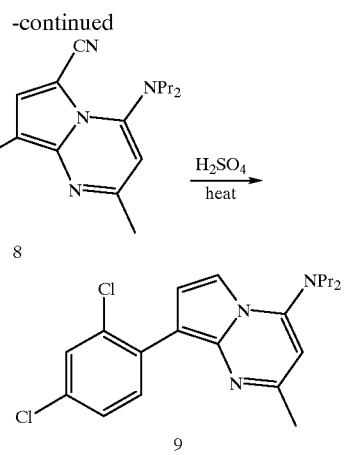

1,1-Dibromo-2-(2,4-dichlorolphenyl)ethene (2)

Into a solution of 2,4-dichlorobenzaldehyde (8.7 g, 50 mmol) and carbon tetrabromide (18.3 g, 55 mmol) in dichloromethane (200 ml) was added portionwise triphenylphosphine (28.8 g, 110 mmol) at 0° C. The slightly yellow mixture was stirred at room temperature for 1 hour and diluted with hexanes (800 ml). This mixture was then filtrated through a short silica gel column with 1:10 ethyl acetate-hexanes and the filtrate was concentrated in vacuo to give a white solid (16.5 g, 100%). recrystallization from ether-hexanes gave a white crystalline product (14.2 g, 86% yield); $^1$H NMR (TMS/CDCl$_3$):

2,4-Dichlorophenylacetylene (3)

A solution of 1,1-dibromo-2-(2,4-dichlorophenyl)ethene (14 g, 42.4 mmol) in THF (100 ml) at −78° C. under nitrogen was treated with butyllithium (1.6 M solution in hexane, 28 ml, 44.8 mmol). after being stirred for 1 hour at −78° C., the reaction mixture was warmed to room temperature and stirred for another hour. The reaction was quenched with water and the product was extracted with hexanes. The extract was dried over MgSO$_4$, filtrated and concentrated in vacuo to give the product. (Corey, E. J.; Fuchs, P. L. *Tetrahedron Lett*. 1972, 3769)

2-Di(trimethylsilyl)amino-3-(2,4-dichlorophenyl)-5-cyanopyrrole (4)

In a 200-ml reaction flask was placed NiCl$_2$ (0.2 g, 1.5 mmol) and then 1N DIBAL-H in hexane (3 ml, 3 mmol) was added. After the color of the catalyst turned to black, Me$_3$SiCN (30 ml, 0.225 mol.) and 2,4-dichlorophenylacetylene (6.4 g, 37.5 mmol) were added to the reaction flask. The mixture was stirred under reflux for 20 hours. The product was isolated by column chromatography (silica gel, hexanes/EtOAc, 5/1) to afford pure 4 (60% yield). (Chatani, N.; Takeyasu, T, Horiuchi, N; Hanafusa, *J. Org. Chem*. 53:3539, 1988)

2-Amino-3-(2,4-dichlorophenyl)-5-cyanopyrrole (5)

A solution of 2-(di(trimethylsilyl)amino-3-(2,4-dichlorophenyl)-5-cyanopyrrole (4, 11.8 g, 30 mmol) in methanol (50 ml) is treated with 2N aqueous hydrochloric acid (30 ml). The mixture is heated to reflux for 1 hour and concentrated in vacuo. The aqueous phase then is basified with solid sodium carbonate and the product is extracted with ethyl acetate. The extract is washed with brine, dried over MgSO$_4$ and concentrated in vacuo to give the product.

1-Cyano-3-(dichlorophenyl)-5-methyl-7-hydroxypyrrolo[1,2-a]pyrimidine (6)

A solution of 2-amino-3-(2,4-dichlorophenyl)-5-cyanopyrrole (5, 5 g, 20 mmol) and ethyl acetoacetate (5.2 g, 40 mmol) in dioxane (50 ml) is heated to reflux overnight.

The cold solution is treated with ether and hexanes and the solid product is collected by vacuo filtration.

1-Cyano-3-(dichlorophenyl)-5-methyl-7-chloropyrrolo[1,2a]pyrimidine (7)

A mixture of 1-cyano-3-(dichlorophenyl)-5-methyl-7-hydroxypyrrolo[1,2-a]pyrimidine (6, 0.64 g, 2 mmol) and POCl$_3$ (3 ml) is heated to reflux for 2 hours. The reaction mixture is hydrolyzed with ice water and the product is extracted with ethyl acetate. The extract was washed with saturated aqueous sodium bicarbonate and brine, dried over MgSO$_4$, filtrated and concentrated in vacuo to afford the product.

1-Cyano-3-(dichlorophenyl)-5-methyl-7-dipropylaminopyrrolo[1,2-a]pyrimidine (8)

A mixture of 1-cyano-3-(dichlorophenyl)-5-methyl-7-chloropyrrolo[1,2-a]pyrimidine (7, 335 mg, 1 mmol) and dipropylamine (1 ml) was heated at 100° C. in a reacti-vial for 2 hours. The product is purified by chromatography on silica gel.

3-(Dichlorophenyl)-5-methyl-7-dipropylaminopyrrolo[1,2-a]pyrimidine (9)

A solution of 1-cyano-3-(dichlorophenyl)-5-methyl-7-dipropylaminopyrrolo[1,2-a]pyrimidine (8, 200 mg, 0.5 mmol) in THF (5 ml) is treated with 2N aqueous H$_2$SO$_4$ (2 ml) and the mixture is heated to reflux for 6 hours. The mixture is neutralized with triethylamine and the product is purified by chromatography on silica gel.

Part B, Pyrrolo[1,2-a]-s-triazines

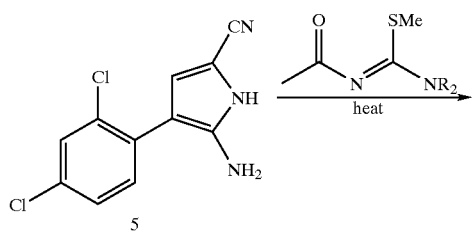

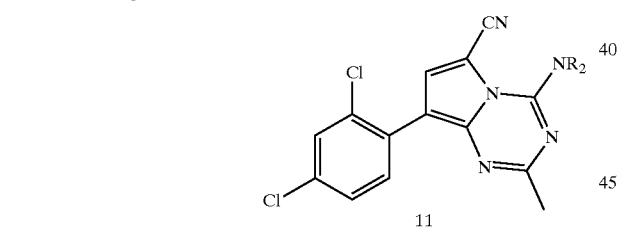

N-Acetyl-N'-propyl-N'-cyclopropanemethyl-S-methylurea (10)

Sodium isothiocyanate (8.9 g, 0.11 mol.) was dissolved in acetone (200 ml) and treated with acetyl chloride (7.8 g, 0.1 mol.) at room temperature. The suspension was stirred at room temperature for 10 minutes before N-propyl-N-cyclopropanemethylamine (11.3 g, 0.1 mol.) was added. This mixture was stirred at room temperature for 15 minutes and MeI (18.5 g, 0.13 mol) and Na$_2$CO$_3$ (13.8 g, 0.11 mol.) were introduced. The mixture was then stirred at room temperature overnight and concentrated in vacuo. The residue was partitioned in ethyl acetate-water. The organic phase was separated and the aqueous phase was extracted with ethyl acetate. The combined organic layer was washed with brine, dried with MgSO$_4$ and concentrated in vacuo to give the product as a yellowish oil. $^1$H NMR: 0.27 (m, 2H), 0.57 m, 2H), 1.08 (m, 1H), 1.68 (m, 2H), 2.17 (s, 3H), 2.38 (s, 3H), 3.39 (d, 2H), 3.51 (t, 2H); MS (ion spray): 229 (M+H).

1-Cyano-3-(dichlorophenyl)-5-methyl-7-dipropylaminopyrrolo[1,2-a]-s-triazine (11)

A mixture of 2-Amino-3-(2,4-dichlorophenyl)-5-cyanopyrrole (5, 0.5 g, 2 mmol) and N,N-dipropyl-N'-acetyl-S-methylthiourea (10, 1.08 g, 5 mmol) is heated at 180° C. in a sealed reacti-vial for 16 hours. Chromatography on silica gel affords the designed product.

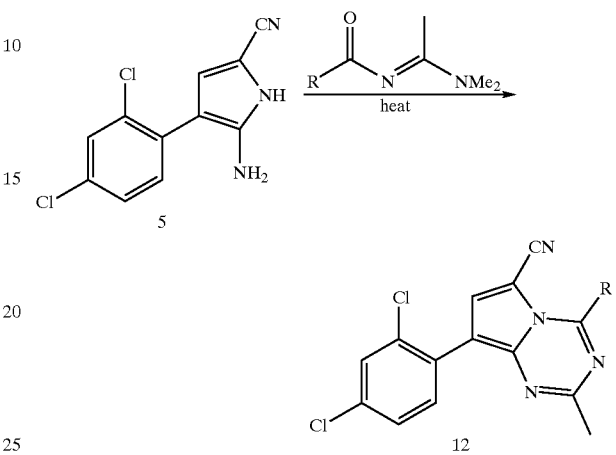

1-Cyano-3-(2,4-dichlorophenyl)-5-methyl-7-(1-ethylpentyl)pyrrolo[1,2-a]-s-triazine (12)

A solution of 2-amino-1-cyano-3-(2,4-dichlorophenyl)-1H-pyrrole (90 mg) and N-dimethyl-N'-(2-ethylhexanoyl)-acetamidine (180 mg) in dioxane (5 ml) was heated to reflux overnight. Chromatography on silica gel with 1:5 ethyl acetate-hexanes gave the title compound.

Example 2

Synthesis of Representative Compounds of Structure (I)

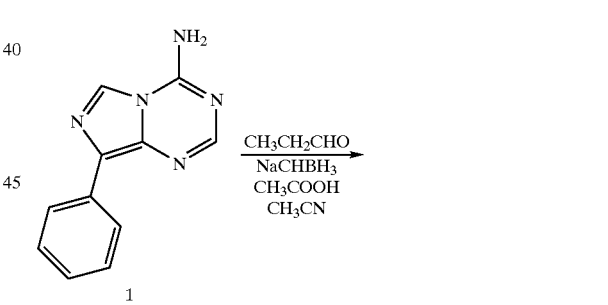

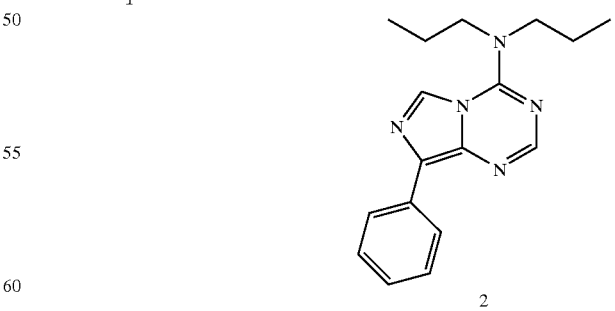

Preparation of 2-Methyl-4-dipropylamino-8-phenyl-imidazo[1,5-a]-1,3,5-triazine (2)

Add sodium cyanoborohydride and then glacial acetic acid (0.1 mL) to a stirring solution of (1) (225 mg, 1 mmol) and propionaldehyde (580 mg. 10 mmol) in acetonitrile (5 mL) at 0° C. Stir the reaction mixture at room temperature for 2 hrs. Patition the reaction mixture between EtOAc and saturated aq. NaHCO₃. Wash the EtOAc layer by Brine, dry under NaSO₄, filter, concentrate to afford a dark residue, which is purified by flash column on silica gel to yield the desired product (2).
(R. Balicki, R. S. Hosmane and N. J. Leonard, *J. Org. Chem.* 48:3, 1983; R. Borch and A. Hassid, *J. Org. Chem.* 37:1673,1972)

Example 3

Synthesis of Representative Compounds of Structure (II)

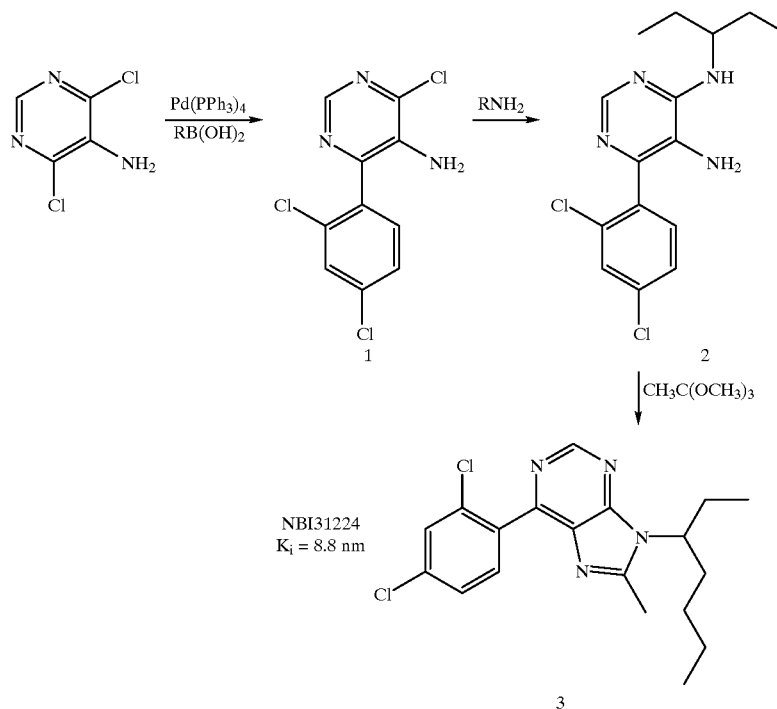

NBI31224
$K_i$ = 8.8 nm

Synthesis of Compound 1

A mixture of 5-Amino-4,6-dichloropyrimidine (1.3 gms, 7.92 mmol), 2,4-Dichlorobenzene boranic acid (1.8 gms, 9.5 mmol), tetrakis triphenylphospine palladium (0.95 mmol), and potassium carbonate (2.12 gms) was partitioned in a mixture of toluene, ethanol, and water (35 ml, 10 ml, 10 ml respectively). The mixture was refluxed under a nitrogen atmosphere for 18 hrs. After reflux, the solution was quenched with 50 ml saturated ammonium chloride and extracted with ethyl acetate (2×300 ml). The organic layers were combined, dried over sodium sulfate and concentrated to yield oil. The crude oil was purified with flash chromatography eluting with hexanes:ethyl acetate (5:1) to yield yellow solid 40% yield. d 4.15 (br, 2H, NH), 7.34 (m, 2H, Ar), 7.53 (s, 1H, Ar), 8.43 (s, 1H, Ar(pyrmidine))ppm.

Synthesis of Compound 2

A mixture of compound 1 (250 mgs, 1.0 mmol) and 3-aminoheptane (0.3 ml) were placed in a 1 ml reaction vial and heated to 130° C. overnight. After overnight, the reaction was cooled and loaded directly on silica prep plate, eluting with hexanes:ether (5:1). Compound was isolated as a solid. δ 0.98 (m, 5H), 1.35 (m, 5H), 1.6 (m, 4H), 3.05 (br, 2H, NH), 4.2 (m, 1H, CH), 4.85 (d, 1H, NH), 7.32 (s, 2H, Ar), 7.49 (s, 1H, Ar), 8.29 (s, 1H, Ar-pyr) ppm. M+H 367.

6-(2,4-Dichlorophenyl)-8-methyl-9-(3-heptanyl)purine (3)

Compound 2 (50 mgs, 0.14 mmol) and triethyl orthoacetate (0.5 ml) were placed in a reaction vial and heated at 110° C. for 10 hrs. After reflux, the reaction was partitioned between ethyl acetate (10 ml) and water (10 ml). The organic layer was extracted, dried over sodium sulfate and all solvent removed. Compound was purified on silica prep plate with hexanes:ether (1:5). 7 mgs isolated. δ 0.91 (m, 5H), 1.30 (m, 5H), 1.9 (m, 4H), 2.63 (s, 3H, methyl), 4.3 (m, 1H, CH), 7.41 (d, 2H, Ar), 7.56 (s, 1H, Ar), 7.64 (d, 1H, Ar), 8.9 (s, 1H, Ar-pyr) ppm. M+H=377.

Example 4

Synthesis of Representative Compounds of

Structure (II)

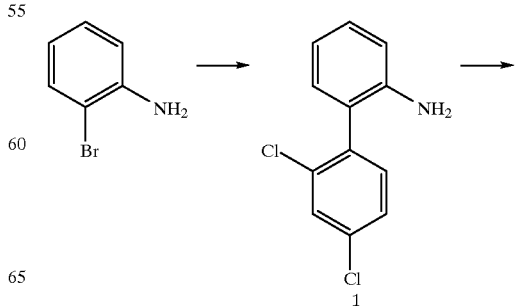

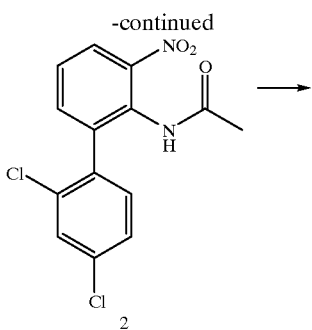

2

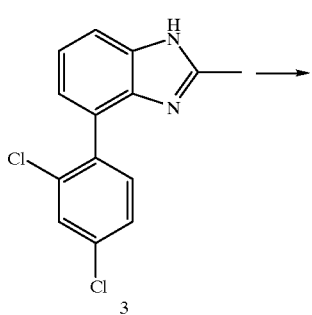

3

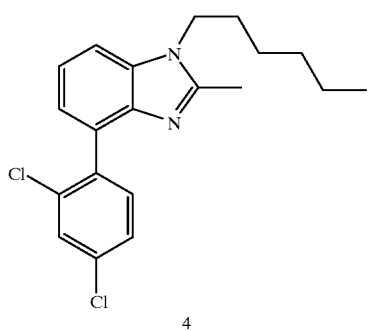

4

2-Amino-6,8-dichlorobiphenyl (1)

A stirred solution of 2-bromoaniline (1.0 g, 5.8 mmol) in 30 mL of toluene was treated with tetrakis(triphenylphosphine)palladium(0) (672 mg, 0.58 mmol, 10% mol) and 2.0M aqueous sodium carbonate solution (8.8 mL, 17.4 mmol). This mixture was treated with dichlorobenzeneboronic acid (2.28 g, 11.0 mmol) ethyl alcohol (8.8 mL). The resulting brown mixture was heated to reflux overnight. The reaction mixture was cooled, diluted with ethyl acetate and washed with saturated ammonium chloride solution once. The organic layer was dried by sodium sulfate, filtered, and concentrated. The residue was purified by flash chromatography on silica gel to provide the desired product (1) (1.0 g, 4.20 mmol, 72%), which was confirmed by GC/MS and $^1$H NMR. GC/MS: m/z=237, 239; 300 MHz $^1$H NMR (CDCl$_3$): δ 3.54 (br s, 2H), 6.78 (d, 1H), 6.84 (d, 1H), 7.01 (d, 1H), 7.19–7.35 (m, 3H), 7.53 (d, 1H).

2-Acetamido-3-nitro-6,8-dichlorobiphenyl (2)

A solution of 2-amino-6,8-dichlorobiphenyl (1) (0.5 g, 2.1 mmol) in 0.5 mL AcOH and 1 mL Ac$_2$O was heated to 100° C. for 15 min., then allowed to come to room temperature. This solution is treated with 90% fuming nitric acid (0.5 mL) and stirred at 5° C. then allowed to warm to room temperature. After the starting material is mostly consumed, the solution is poured into water and the crude product is isolated by extraction with ethyl acetate. Flash chromatography using silica gel and ethyl acetate/hexane gives the desired title compound.

1-Methyl-4-(2',4'-dichlorophenyl)benzimidazole (3)

A solution of 2-Acetamido-3-nitro-6,8-dichlorobiphenyl (2) (2.1 mmol) in 10 mL AcOH, is treated with 100 mg of 10% Pd/C and shaken under an atmosphere of hydrogen until the starting material is ca. 95% consumed. The mixture is filtered then heated to 100° C. until the cyclization is ca. 90% complete, then allowed to come to room temperature. This solution is poured into water and the title product isolated by filtration. This product is then purified by flash chromatography on silica using ethyl acetate/hexanes.

1-Methyl-4-(2',4'-dichlorophenyl)-N-hexylbenzimidazole (4)

A solution of 1-methyl-4-(2',4'-dichlorophenyl)benzimidazole (3) (1 mmol) in 1 mL DMF, is treated with 300 mg of hexyl chloride and cesium chloride (2 mmole) then stirred under nitrogen. After 16 hours this solution is poured into water and the product isolated by extraction with ethyl acetate. The title compound is then purified by flash chromatography on silica, using ethyl acetate/hexanes.

Example 5

Synthesis of Representative Compounds of Structure (II)

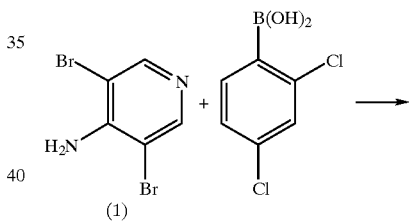

(1)

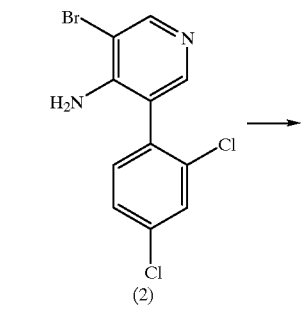

(2)

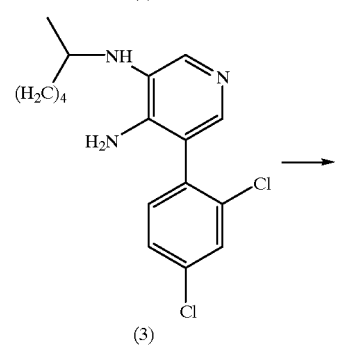

(3)

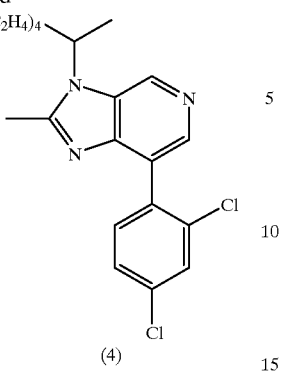

(4)

3-bromo-5-(3,4-dichlorophenyl)-4-amino-pyridine (2):

A solution of 3,5-dibromo-4-amino-pyridine 1 (4.0 g, 15.87 mmol), Pd(PPh$_3$)$_4$ (0.91 g, 0.78 mmol) and aqueous solution of Na$_2$CO$_3$ (23.8 ml, 2M) in toluene (80 ml) is added to a solution of dichlorobenzene boronic acid (6.23 g, 46.4 mmole) in ethanol (24 ml). The mixture is refluxed for 14 h., diluted with ethyl acetate and washed with saturated NH$_4$Cl solution. The organic layer is dried over sodium sulfate and concentrated in vacuo. The residue is chromatographed on silica gel to give 2.

5-(3,4-dichlorophenyl)-3-aminoheptane-4-amino-pyridine (3):

A mixture of 2 (1 mmol), 3-aminoheptane (1.2 mmol), Pd$_2$(DBA)$_3$ (0.02 mmol, 4 mol % Pd, 18 mg), BINP (0.04 mmol, 25 mg), NaOtBu (1.4 mmol, 134 mg), and toluene (0.11 M with 3-bromopyridine, 9 ml) is heated to 70° C. under nitrogen until 2 is consumed. The reaction is then cooled to room temperature, and taken up in 10 ml diethyl ether, washed 3 times with 10 ml saturated brine, dried over MgSO$_4$, and condensed in vacuo. The crude product is purified by flash chromatography to afford 3.

7-(3,4-dichlorophenyl)-2-methyl-3-(3-aminoheptane)-(4,6-c)-imidazo-pyridine (4):

A mixture of 3 (0.14 mmol) and triethyl orthoacetate (0.5 ml) is heated at 110° C. in reaction vial over night. The mixture is dissolved in ethyl acetate (10 ml), washed with water, dried over sodium sulfate and concentrated in vacuo. The crude product is purified by flash chromatography to afford 4.

Example 6

Synthesis of Representative Compounds of Structure (II)

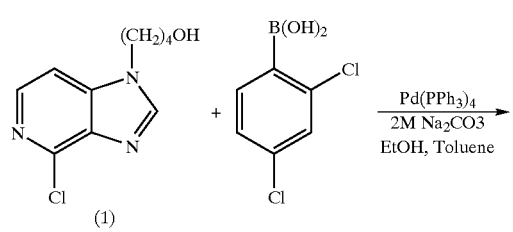

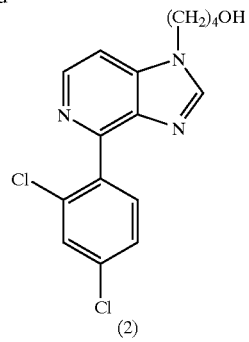

(2)

4-(2,4-dichlorophenyl)-1-(4-hydroxyl-butyl)-imidazo-(4,5-c)-pyridine (2):

A solution of (1)[1] (1.0 g, 4.43 mmol), Pd(PPh$_3$)$_4$ (0.23 g, 0.22 mmol) and aqueous solution of Na$_2$CO$_3$ (6.6 ml, 2M) in toluene (25 ml) is added to a solution of dichlorobenzene boronic acid (1.74 g, 8.86 mmol) in ethanol (7 ml). The mixture is refluxed for 14 h., diluted with ethyl acetate and washed with saturated NH$_4$Cl solution. The organic layer is dried over sodium sulfate and concentrated in vacuo. The residue is chromatographed on silica gel to give 2.

(Ronald T. Borchardt et al., *J Med. Chem.* 28:467–471, 1985)

Example 7

Synthesis of Representative Compounds of Structure (II)

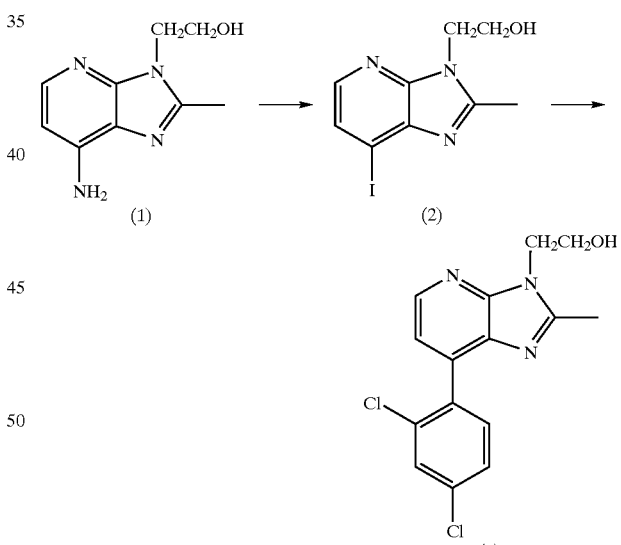

2-Iodo-7-methyl-6-ethanol-(4,5-b)-imidazo-pyridine (2):

To a solution of (1)[1] (1.12 mmol) in 2N HCl (8 ml) is added at ice bath temperature sodium nitrite (84 mg, 1.2 mmol) in water (4 ml). The mixture is stirred at ice bath temperature for 15 min. and added dropwise to a solution of potassium iodide (340 mg, 2.08 mmol) in water (4 ml). The reaction is heated to 60° C. for 1 h. The solution is basified with 2M NaOH and extracted with ethyl acetate, washed with brine and concentrated in vacuo. the residue is purified by chromatography on silica gel to give the product 2.

2-(2,4-dichlorophenyl)-7-methyl-6-ethanol-(4,5-b)-imidazo-pyridine (3):

A solution of (2) (4.43 mmol), Pd(PPh₃)₄ (0.22 mmol) and aqueous solution of Na₂CO₃ (6.6 ml, 2M) in toluene (25 ml) is added to a solution of dichlorobenzene boronic acid (8.86 mmol) in ethanol (7 ml). The mixture is refluxed for 14 h., diluted with ethyl acetate and washed with saturated NH₄Cl solution. The organic layer is dried over sodium sulfate and concentrated in vacuo. The residue is chromatographed on silica gel to give 3.
(Ramsden, Christopher A. J., *Chem. Soc. Perkin Trans.* 21:2789–2812, 1992).

Example 8

Synthesis of Representative Compounds of Structure (III)

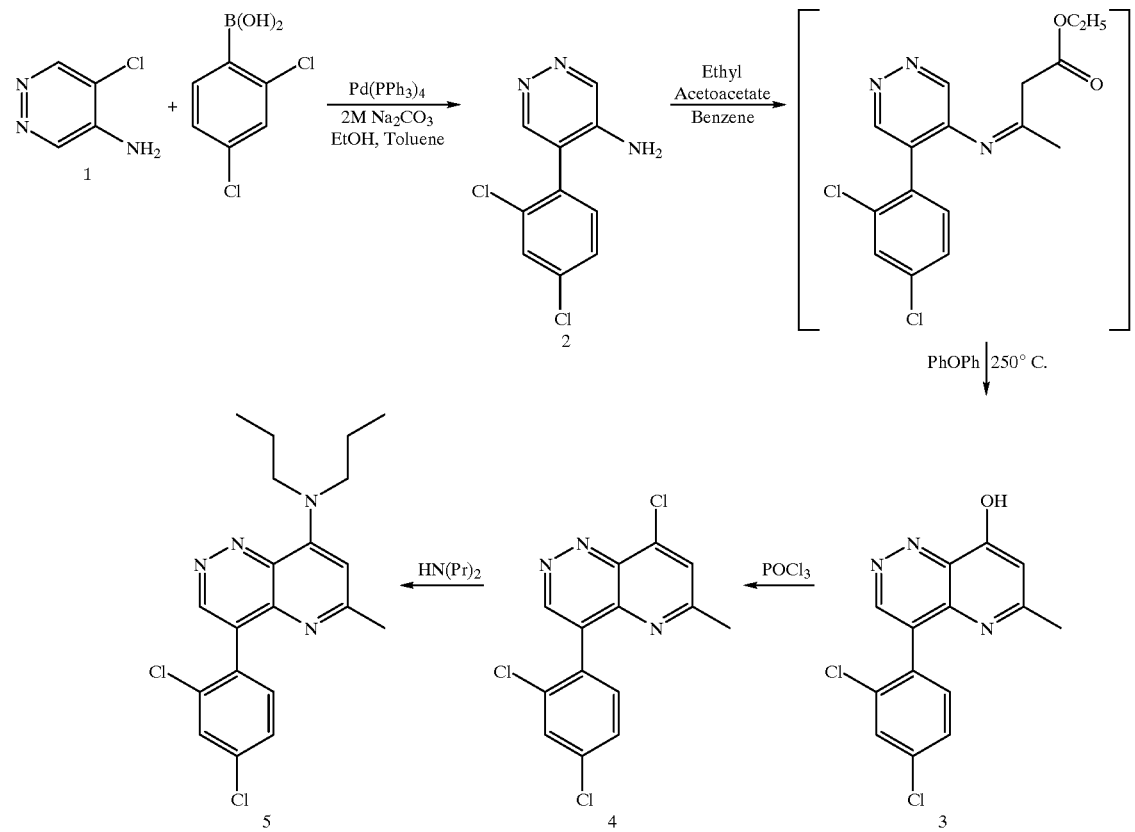

4-Amino-5-(3,4-dichlorophenyl)pyridizine (2)

To a solution of 4-amino-5-choloropyridizine (1) (3.25 g, 25 mmol) in toluene (100 mL) under argon add tetrakis (triphenylphosphine)palladium(0) (2.9 g. 2.5 mmol), 2M aqueous sodium carbonate (35 mL) (degassed) and a solution of dicholorobenzeneboronic acid (5.3 g, 27 mmol) in ethanol (35 ml) (degassed). Heat the resulting two phase mixture for 16 hours at reflux under argon. Dilute the reaction with ethyl acetate (50 mL) and wash the organic layer with saturated ammonium chloride, dry (Na₂SO₄) and evaporate to dryness in vacuo. Purify by flash chromatography and isolate the desired product 2 by combining the appropriate fractions and evaporating to dryness.
2-Methyl-4-hydroxy-8-(3,4-dichlorophenyl)pyrido[2,3-c]pyridazine (3)

Reflux a solution of 4-amino-5-(3,4-dichlorophenyl) pyridazine (2) (4.8 g, 20 mmol), ethyl acetoacetate (2.7 g, 20 mmol) and p-toluenesulfonic acid monohydrate (20 mg) in benzene (100 mL) for 30 minutes. Cool the reaction mixture to ambient temperature and purify the intermediate product by flash chromatography. Add a solution of the intermediate (3.5 g, 10 mmol) in 5 mL of diphenyl ether to 10 mL of diphenyl ether at 240° C. and reflux for 5 minutes. Cool the reaction and collect the resulting solid by filtration. Wash the product 3 with ether and dry.
2-Methyl-4-chloro-8-(3,4-dichlorophenyl)pyrido[2,3-c] pyridazine (4)

Reflux a mixture of 2-methyl-4-hydroxy-8-(3,4-dichlorophenyl)pyrido[2,3-c]pyridazine (3) (3.0 g, 10 mmol) in phosphorous oxychloride (10 mL) for 2 hrs. Cool the reaction mixture, pour onto cracked ice and neutralize the solution with 1N NaOH. Extract the solution with ethyl acetate (2×100 mL) and wash the combined organic layers with brine. Dry the solution (Na₂SO₄) and evaporate in vacuo to obtain 4.
2-Methyl-4-dipropylamino-8-(3,4-dichlorophenyl)pyrido[2, 3-c]pyridazine (5)

Heat a mixture of 2-methyl-4-chloro-8-(3,4-dichlorophenyl)pyrido[2,3-c]pyridazine (4) (1.0 g, 3.1 mmol) and p-toluenesulfonic acid (1.6 g) in 5 mL of di-n-propylamine in a sealed tube at 180° C. for 48 hours. Cool the reaction mixture to ambient temperature and partition between ethyl acetate and water. Wash the organic layer with water and dry over MgSO₄. Evaporate the dried solution and purify the desired product 5 by flash chromatography.
(T. Kuraishi, R. N. Castle, *J. Heterocyclic Chem.* 1:42, 1964)

Example 9

Synthesis of Representative Compounds of Structure (III)

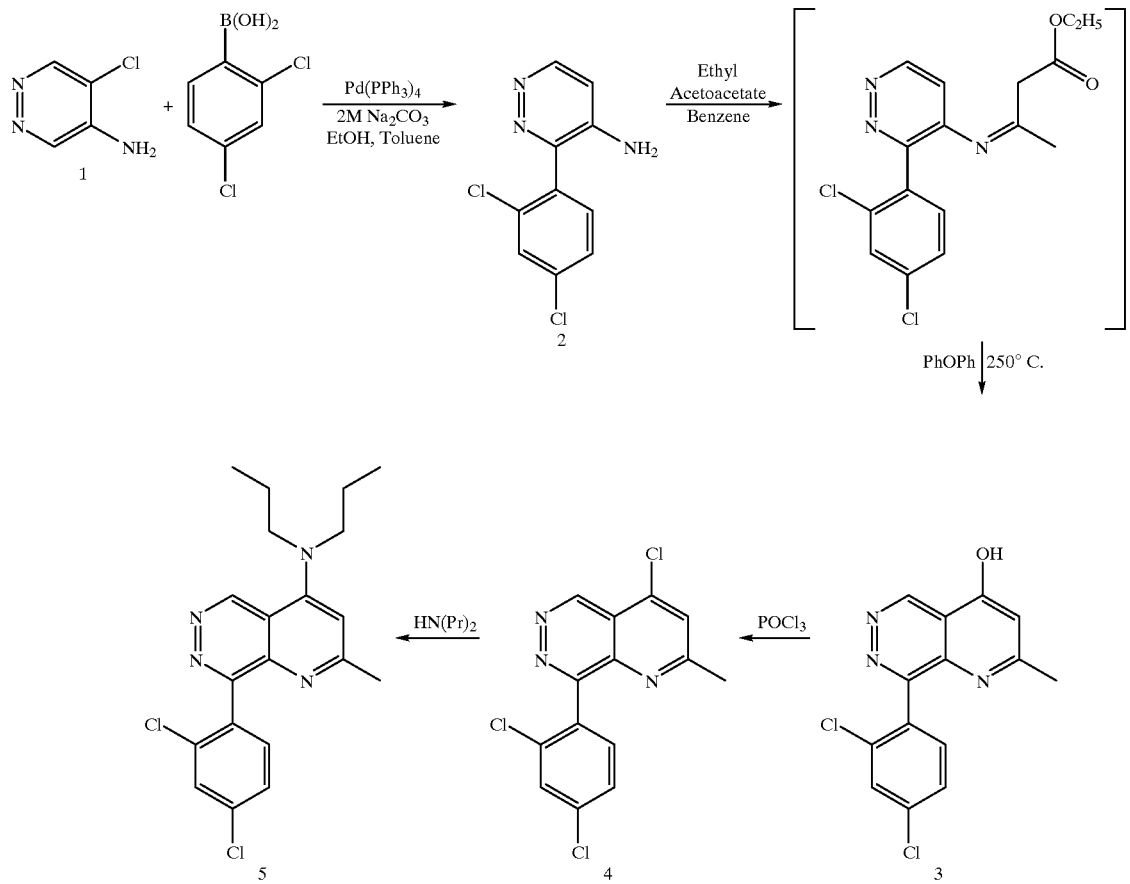

3-(3,4-Dichlorophenyl)-4-aminopyridizine (2)

To a solution of 4-amino-3-choloropyridizine (1) (6.5 g, 50 mmol) in toluene (200 mL) under argon add tetrakis (triphenylphosphine)palladium(0) (5.8 g. 5 mmol), 2M aqueous sodium carbonate (75 mL) (degassed) and a solution of dicholorobenzeneboronic acid (10.6 g, 54 mmol) in degassed ethanol (75 ml). Heat the two phase mixture for 16 hours at reflux under argon. Dilute the reaction with ethyl acetate (100 mL) and wash the organic layer with saturated ammonium chloride, dry ($Na_2SO_4$) and evaporate to dryness in vacuo. Purify by flash chromatography and isolate the desired product 2 by combining the appropriate fractions and evaporating them to dryness.

2-Methyl-4-hydroxy-8-(3,4-dichlorophenyl)pyrido[2,3-d]pyridazine (3)

Reflux a solution of 3-(3,4-dichlorophenyl)-4-aminopyridizine (2) (7.2 g, 30 mmol), ethyl acetoacetate (4.0 g, 30 mmol) and of p-toluenesulfonic acid monohydrate (30 mg) in benzene (150 mL) for 30 minutes. Cool the reaction mixture to ambient temperature and purify the intermediate product by flash chromatography. Add a solution of the intermediate (5.25 g, 15 mmol) in 10 mL of diphenylether to 15 mL of diphenylether at 240° C. and reflux for 5 minutes. Cool the reaction and collect the resulting solid (3) by filtration. Wash the product 3 with ether and dry.

2-Methyl-4-chloro-8-(3,4-dichlorophenyl)pyrido[2,3-d]pyridazine (4)

Reflux a mixture of 2-methyl-4-hydroxy-8-(3,4-dichlorophenyl)pyrido[2,3-d]pyridazine (3) (4.5 g, 15 mmol) in phosphorous oxychloride (15 mL) for 2 hrs. Cool the reaction mixture, pour onto cracked ice and neutralize the solution with 1N NaOH. Extract the solution with ethyl acetate (2×100 mL) and wash the combined organic layers with brine. Dry the solution ($Na_2SO_4$) and evaporate in vacuo to obtain 4.

2-Methyl-4-dipropylamino-8-(3,4-dichlorophenylpyrido[2,3-d]pyridazine (5)

Heat a mixture of 2-methyl-4-chloro-8-(3,4-dichlorophenyl)pyrido[2,3-d]pyridazine (4) (2.0 g, 6.2 mmol) and p-toluenesulfonic acid (3.2 g) in 10 mL of di-n-propylamine in a sealed tube at 180° C. for 48 hours. Cool the reaction mixture to ambient temperature and partition the reaction mixture between ethyl acetate and water. Wash the organic layer with water and dry over $MgSO_4$. Evaporate the dried solution and purify the product 5 by flash chromatography.

(D. E. Kiinge, H. C. van der Plas, G. Geurtsen, A. Koudijs, *Recl. Trav. Chim. (Pays-Bas)* 93:236, 1974)

Example 10

Synthesis of Representative Compounds of Structure (III)

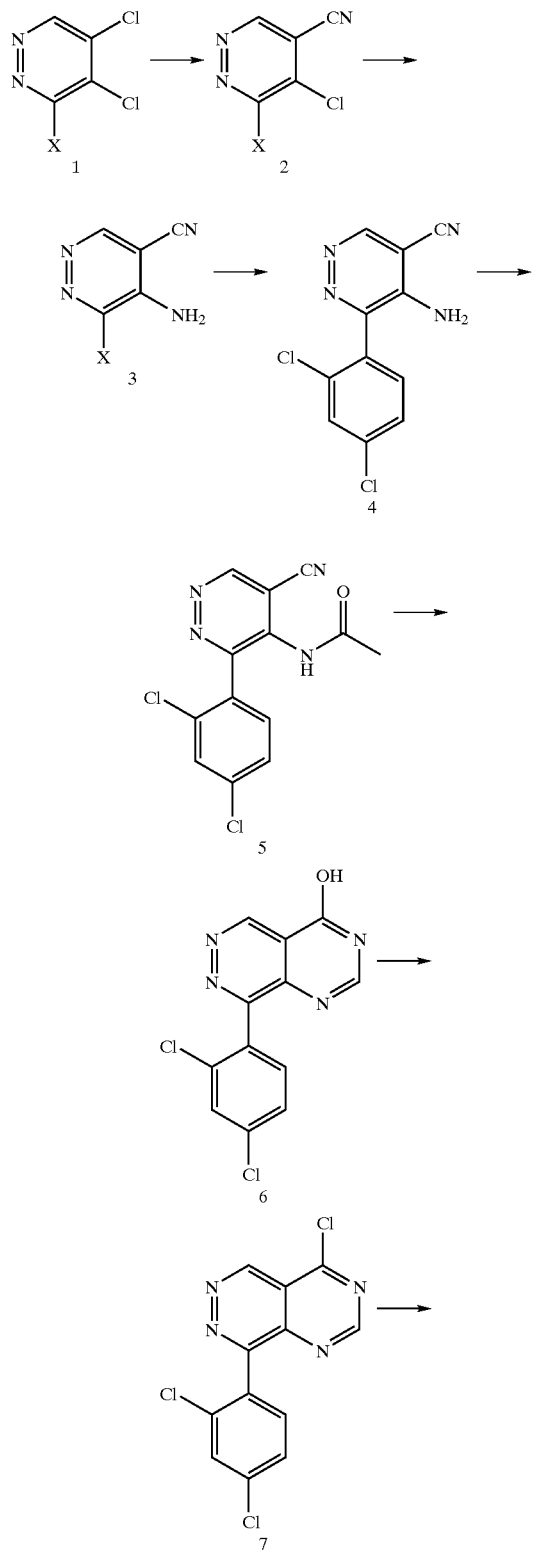

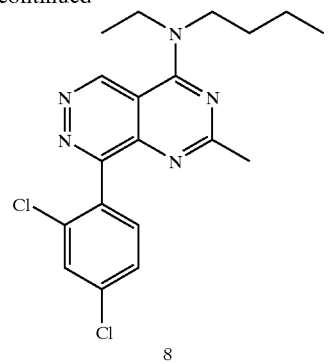

Compound 2

Compound 2 is synthesized by refluxing a mixture of compound 1 (X=Cl, Br) 10.0 mmol), sodium cyanide (3.0 gms), aluminium oxide (2.8 gms) and tetrakistriphenylphosphine palladium (1.0 mmol) in toluene (100 ml) under a nitrogen atmosphere. After refluxing overnight, the mixture is cooled and partitioned between ethyl acetate and water. The organic layers are dried over sodium sulfate and the solvent removed under vacuum. The compound is purified by, for example, flash chromatography eluting with a mixture of ethyl acetate and hexane.

Compound 3

Compound 3 is synthesized by heating 2 (9.0 mmol) in a solution of ammonia in a Parr bomb at 150° C. The solution is concentrated on rotary evaporator and the crude solid purified by for example recrystallization or flash chromatography eluting with hexanes:ethyl acetate to give product 3.

Synthesis of Compound 4

A mixture of 3 (8 mmol), and a suitable boronic acid such as: 2,4-Dichlorobenzene boronic acid (1.8 gms, 9.5 mmol), tetrakis(triphenylphospine)palladium (0.95 mmol), and potassium carbonate (2.12 gms) is partitioned in a mixture of toluene, ethanol, and water (35 ml. 10 ml, 10 ml respectively). The mixture is refluxed under a nitrogen atmosphere for 18 hrs. After reflux, the solution is quenched with 50 ml saturated ammonium chloride and extracted with ethyl acetate. The organic layers are combined, dried over sodium sulfate and concentrated to yield oil. The crude oil is purified with flash chromatography eluting with, for example, hexanes:ethyl acetate to yield 4.

Compound 6

Compound 5 is synthesized by heating 4 (2.38 gms, 9.0 mmole) in acetic anhydride (10 mmole) and acetic acid (20 mL) for 2 hours. After reflux, the resulting solution of 5 is concentrated down on rotary evaporator and the crude solid is dissolved up in phosphoric acid (85%, 10 ml). The solution is refluxed for 0.5 hours and poured over ice. A solid precipitates and is collected by filtration to leave compound 6.

Compound 7

Compound 6 (10 mmole) and 3 mL of $POCl_3$ are mixed and heated to 100° C. until most of the starting material is consumed, then allowed to cool to r.t., and poured into 5% $NaHCO_3$. This is extracted with EtOAc, the organic phase is ished with brine, dried and concentrated. The product is purified by flash chromatography ($SiO_2$) using, for example, ethyl acetate/hexane, to give title compound.

2-Methyl-4-(dipropylamino)-8-(2,4-dichlorophenyl)pyridazino[4,5-d]pyrimidine (8):

Compound 7 (10 mmoles) and a secondary amine such as dipropylamine (100 mmoles) and 75 mL acetonitrile are refluxed for several hours until most of the chloro derivative is consumed. The reaction is poured into water and extracted with ethyl acetate. The organic phase is ished with water, then brine, dried (MgSO$_4$) and concentrated. The resulting residue is purified by flash chromatography (SiO$_2$) using, for example, ethyl acetate/hexane, to give title compound.

Example 11

Synthesis of Representative Compounds of Structure (IV)

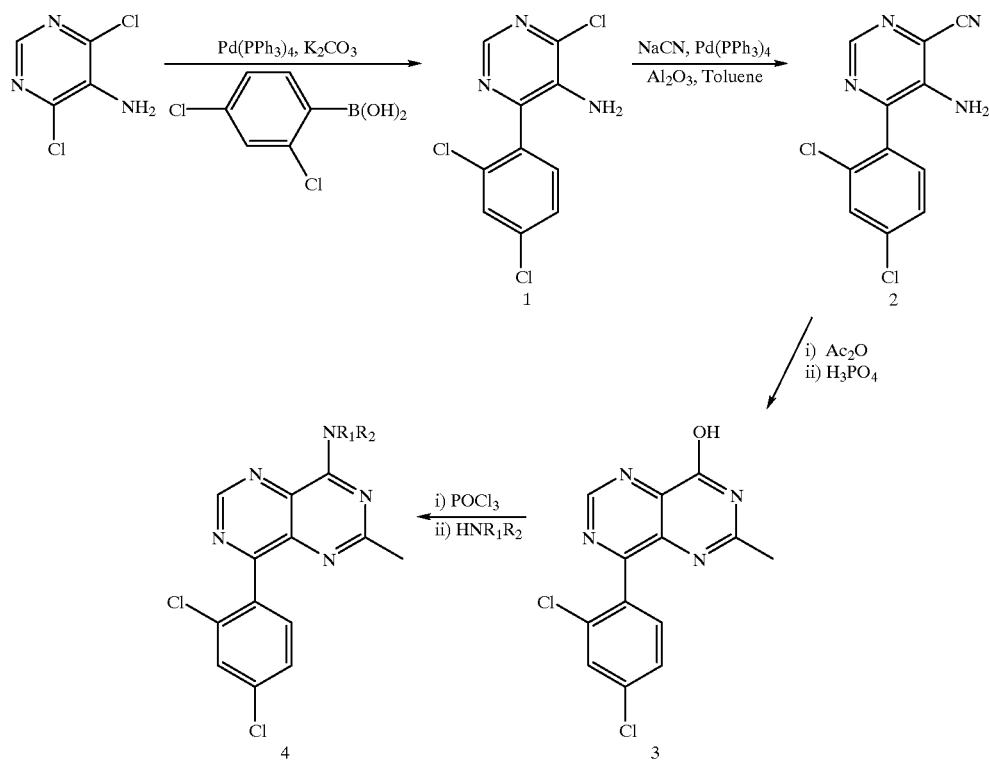

Synthesis of Compound 1

A mixture of 5-Amino-4,6-dichloropyrimidine (1.3 gms, 7.92 mmol), 2,4-Dichlorobenzene boranic acid (1.8 gms, 9.5 mmol), tetrakis triphenylphospine palladium (0.95 mmol), and potassium carbonate (2.12 gms) was partitioned in a mixture of toluene, ethanol, and water (35 ml, 10 ml, 10 ml respectively). The mixture was refluxed under a nitrogen atmosphere for 18 hrs. After reflux, the solution was quenched with 50 ml saturated ammonium chloride and extracted with ethyl acetate (2×300 ml). The organic layers were combined, dried over sodium sulfate and concentrated to yield oil. The crude oil was purified with flash chromatography eluting with hexanes:ethyl acetate (5:1) to yield yellow solid. 40% yield. δ 4.15 (br, 2H, NH), 7.34 (m, 2H, Ar), 7.53 (s, 1H, Ar), 8.43 (s, 1H, Ar(pyrmidine))ppm.

Compound 2

Compound 2 is synthesized by refluxing a mixture of compound 1 (2.73 gms, 10.0 mmol), sodium cyanide (3.0 gms), aluminium oxide (2.8 gms) and tetrakistriphenylphosphine palladium (1.0 mmol) in toluene (100 ml) under a nitrogen atmosphere. After refluxing overnight, the mixture is cooled and partitioned between ethyl acetate and water. The organic layers are dried over sodium sulfate and all solvent removed. The compound is purified by flash chromatography eluting with a hexane:ethyl acetate mixture.

Compound 3

Compound 3 is synthesized by refluxing 2 (2.38 gms, 9.0 mmol) in acetic anhydride (20 ml) for 2 hours. After reflux, the solution is concentrated down on rotary evaporator and the crude solid is dissolved up in phosphoric acid (85%, 10 ml). The solution is refluxed for 0.5 hours and poured over 200 ml of ice. A white solid crashes out of the solution and is collected by filtration to leave pure compound 3.

2-Methyl-4-dipropylamino)-8-(2,4-dichlorophenyl)pyrimidino[5,4-d]pyrimidine (4)

A suspension of compound 3 (2.44 gms, 8.0 mmol) in phosphorous oxychloride (5 ml) is refluxed for one hour. After reflux, the dark solution is concentrated on high vacuum pump to yield a crude dark solid. This crude solid is then dissolved up in 20 ml acetonitrile and refluxed in the presence of excess dipropyl amine. After two hours, the reaction is stopped and the solution is partitioned between ethyl acetate and sodium bicarbonate solution. The organic layers are separated and dried over sodium sulfate. All solvent is removed and the compound is purified by flash chromatography by eluting with hexanes:ether.

Example 12

Synthesis of Representative Compounds of Structure (IV)

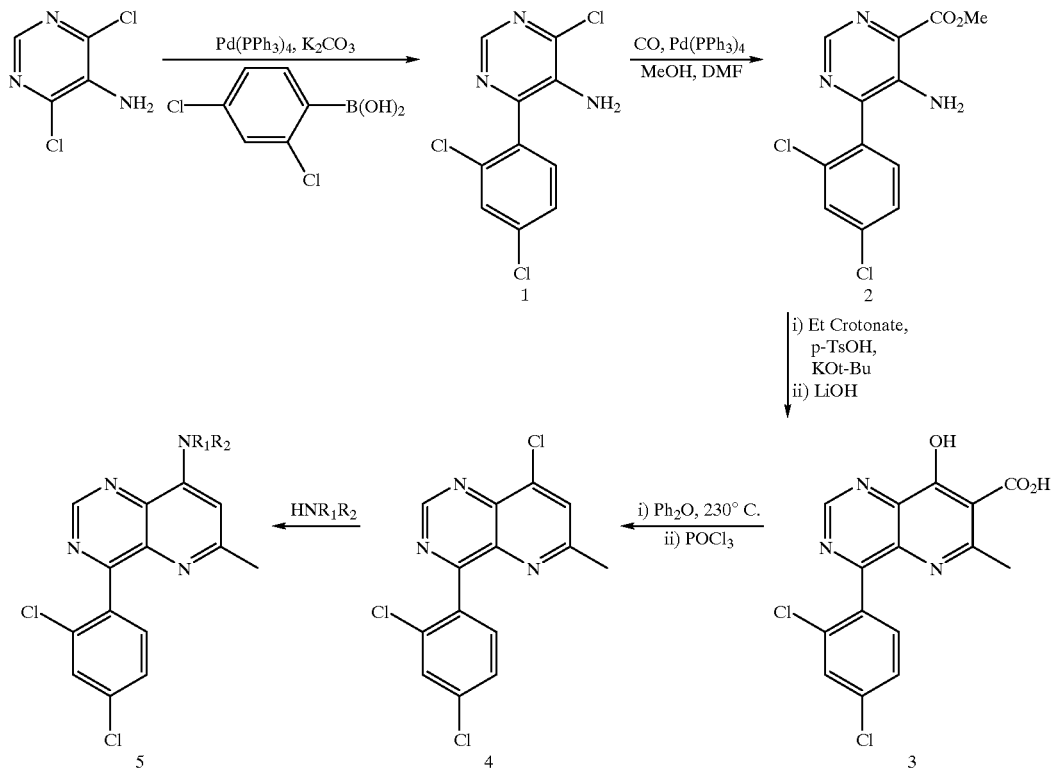

Synthesis of Compound 1

A mixture of 5-Amino-4,6-dichloropyrimidine (1.3 gms, 7.92 mmol), 2,4-Dichlorobenzene boranic acid (1.8 gms, 9.5 mmol), tetrakis triphenylphospine palladium (0.95 mmol), and potassium carbonate (2.12 gms) was partitioned in a mixture of toluene, ethanol, and water (35 ml, 10 ml, 10 ml respectively). The mixture was refluxed under a nitrogen atmosphere for 18 hrs. After reflux, the solution was quenched with 50 ml saturated ammonium chloride and extracted with ethyl acetate (2×300 ml). The organic layers were combined, dried over sodium sulfate and concentrated to yield oil. The crude oil was purified with flash chromatography eluting with hexanes:ethyl acetate (5:1) to yield yellow solid. 40% yield. d 4.15 (br, 2H, NH), 7.34 (m, 2H, Ar), 7.53 (s, 1H, Ar), 8.43 (s, 1H, Ar(pyrmidine))ppm.

Compound 2

Compound 2 is synthesized by heating a mixture of compound 1 (2.73 gms, 10.0 mmol), and tetrakistriphenylphosphine palladium (1.0 mmol) in a methanol and DMF mixture under a carbon monoxide atmosphere (50 psi) in a Parr bomb at 100° C. for 12 hours. The mixture is cooled and partitioned between ethyl acetate and water. The organic layers are dried over sodium sulfate and all solvent removed. The compound is purified by flash chromatography eluting with a hexane:ethyl acetate mixture.

Compound 3

A solution of 2 (1 gm, 3.36 mmol) and ethoxy crotonate (1.5 g, 5.2 mmole) and 75 mg p-toluenesulfonic acid monohydrate in 50 mL xylene is stirred and heated to reflux under $N_2$. Solvent (25 mL) is removed by slow distillation over 1 h. The solution is allowed to cool to r.t. and a solution of potassium t-butoxide (570 mg, 5.1 mmole) in 12 mLs of absolute ethanol is added to the mixture. This mixture is heated to 80° C. for 2 h. This is allowed to cool to r.t., and treated with 0.6 mL AcOH, then concentrated to dryness.

The residue is suspended in EtOAc stirred, filtered and washed to remove all the product from the KOAc. The filtrate is concentrated to a small volume and used crude. A solution of the crude mixture, ethyl ester (1.7 g, 4.8 mmole) and 17.5 mL of 1 M LiOH in 10 mL ethanol is stirred and heated to reflux under $N_2$ for 16 h. The solution is then allowed to cool to r.t. and poured into a mixture of 15 mLs of 1M hydrochloric acid in 100 mLs of water. This solution is extracted with EtOAc, the organic phase washed with brine, dried and concentrated to give the title compound 3.

Compound 4

A solution of 3 (400 mg, 1.2 mmole) in 0.4 mL diphenyl ether is stirred and heated to 230° C. for 1.5 h. The solution is then allowed to cool to r.t and 0.8 mL of $POCl_3$ added. This mixture is heated to 100° C. for 2 h, then allowed to cool to r.t., and poured into 5% $NaHCO_3$. This is extracted with EtOAc, the organic phase washed with brine, dried and concentrated. The product is purified by flash chromatography ($SiO_2$) using 0 to 10% ether/hexane, to give compound 4.

2-Methyl-4-(dipropylamino)-8-(2,4-dichlorophenyl)pyrido[3,2-d]pyrimidine (5. R1=R2=nPr)

A mixture of 4 (10 mg), p-toluenesulfonic acid (20 mg) and dipropylamine (50 ml) is stirred and heated to 195° C. in a sealed tube for 1.5 h. The solution is then allowed to cool to r.t., and dissolved in a mixture of water and EtOAc. This is extracted with EtOAc, the organic phase washed with brine, dried and concentrated. The product is purified by prep. TLC ($SiO_2$) using ethyl acetate/hexane.

Example 13

Synthesis of Representative Compounds of Structure (V)

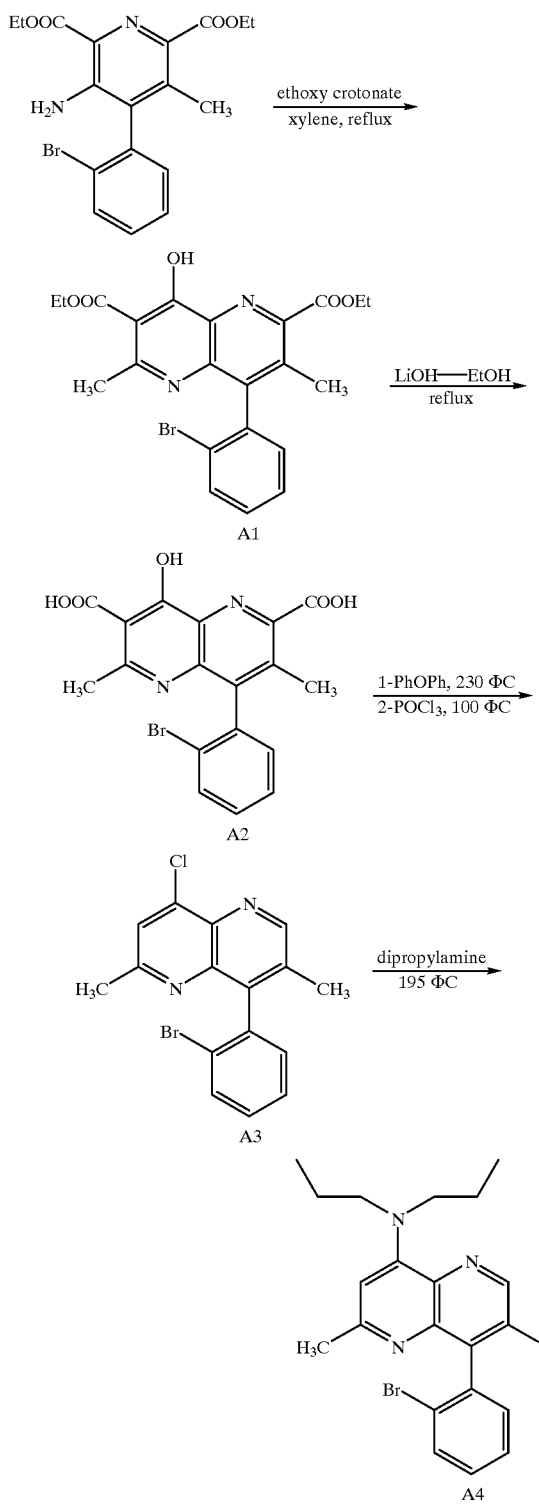

A1

A2

A3

A4

2,7-dimethyl-3,6-dicarboxy-4-hydroxy-8-(2'-bromophenyl)-1,5-naphthyridine, ethyl ester (A1):

A solution of 2,6-carboxy-3-amino-4-(2'-bromophenyl)-5-methyl pyridine, ethyl ester[1] (2.11 g, 5.2 mmole), ethoxy crotonate (1.0 equivalent) and p-toluenesulfonic acid monohydrate (75 mg) in xylene (50 ml) is stirred and heated to reflux under $N_2$. Solvent (25 ml) is removed by slow distillation over 1 h. The solution is allowed to cool to r.t. and a solution of potassium t-butoxide (570 mg, 5.1 mmole) in absolute ethanol (12 ml) is added. This mixture is heated to 80° C. for 2 h. This is allowed to cool to r.t., treated with AcOH (0.6 ml) then concentrated to dryness. The residue is suspended in EtOAc stirred, filtered and washed to remove all the product from the KOAc. The filtrate is concentrated to a small volume and treated with ethyl ether to precipitate the product A1.

2,7-dimethyl-3,6-carboxy-6-hydroxy-8-(2'-bromophenyl)-1,5-naphthyridine (A2):

A solution 2,7-dimethyl-3,6-dicarboxy-4-hydroxy-8-(2'-bromophenyl)-1,5-naphthyridine, ethyl ester (2.21 g, 4.8 mmole) and LiOH (17.5 ml, 1M) in ethanol (10 ml) is stirred and heated to reflux under $N_2$ for 16 h. The solution is allowed to cool to r.t. then poured into a mixture of hydrochloric acid (15 ml, 1M) in water (100 ml). This is extracted with EtOAc, the organic phase is washed with brine, dried and concentrated to give the title compound. This is used directly in the next step.

2,7-methyl-4-chloro-8-(2'-bromophenyl)-1,5-nanhthyridine (A3):

A solution of 2,7-dimethyl-3,6-carboxy-6-hydroxy-8-(2'-bromophenyl)-1,5-naphthyridine (0.5 g, 1.2 mmole) in diphenyl ether (0.4 ml) is stirred and heated to 230° C. for 1.5 h. The solution is allowed to cool to r.t and $POCl_3$ (0.8 ml) is added. This mixture is heated to 100° C. for 2 h, then allowed to cool to r.t., and poured into 5% $NaHCO_3$. This is extracted with EtOAc, the organic phase washed with brine, dried and concentrated. The product is purified by flash chromatography on silica gel to give the title compound.

2,7-dimethyl-4-dipropylamino-8-(2'-bromophenyl)-1,5-naphthyridine (A4):

A mixture of 2,7-methyl-4-chloro-8-(2'-bromophenyl)-1,5-naphthyridine (10 mg, 0.02 mmole), p-toluenesulfonic acid (20 mg) and dipropylamine (50 μl) is stirred and heated to 195° C. for 1.5 h. The solution is allowed to cool to r.t., then dissolved in a mixture of water and EtOAc. This is extracted with EtOAc, the organic phase washed with brine, dried and concentrated. The product is purified by prep. TLC ($SiO_2$) using ethyl acetate/hexane, to give the product.

(Dale L. Boger, Steven R. Duff, James S. Panek, Masami Yasuda, *J. Org. Chem.* 50:5782–5789, 1985)

Example 14

Synthesis of Representative Compounds of Structure (V)

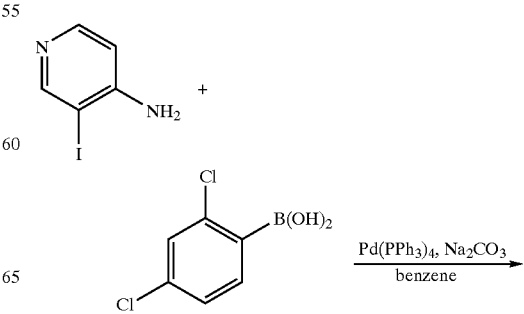

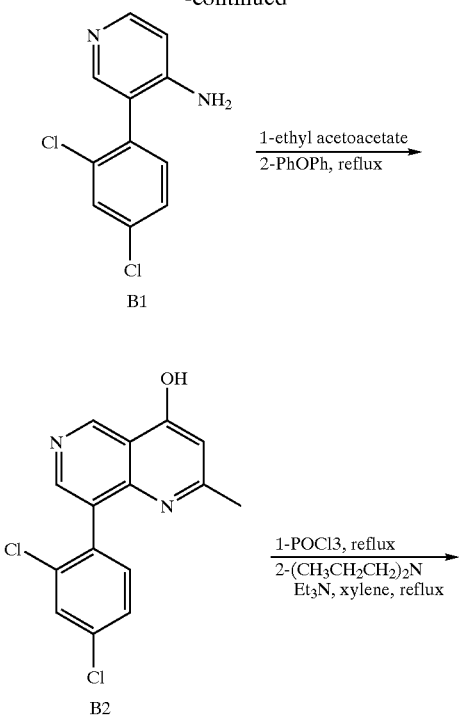

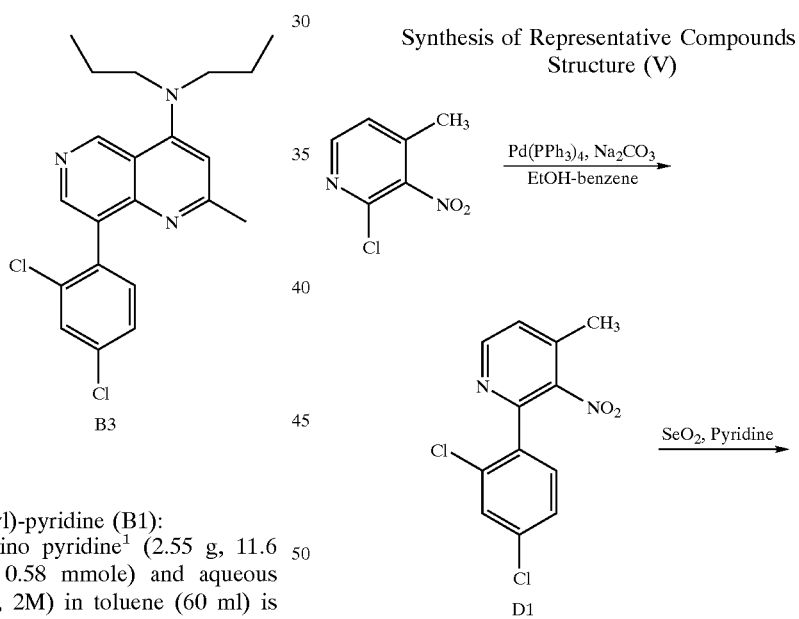

poured into high boiling petroleum ether with vigorous stirring. The resulting solid formed is filtered off and washed with diethyl ether to give the product B2.

2-methyl 4-diprolylamino-8-(2',4'-dichlorophenyl)-1,6-naphthyridine (B3):

A mixture of B2 (0.10 mg, 0.32 mmole) and phosphorous oxychloride (0.5 ml) is heated at reflux for 6 h. Excess reagent is removed in vacuo and the residual compound is treated with dipropyl amine (100 mg) and triethylamine (100 mg) in xylene (2 ml) and the mixture is refluxed for 14 h. The solution is poured into ethyl acetate and washed with dilute bicarbonate solution, the organic layer is dried and the solvent removed in vacuo. The residue is chromatographed on silica gel to afford B3.

(L. Estel, F. Marsais, G. Queguiner, *J. Org. Chem.* 53:2740–2744, 1988)

Example 15

Synthesis of Representative Compounds of Structure (V)

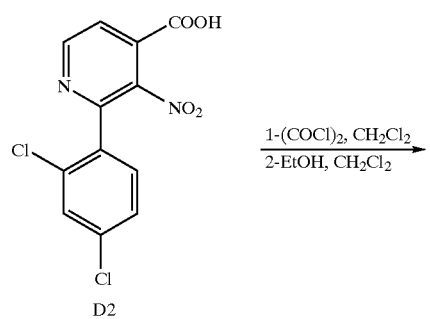

4-amino-3-(2',4'-dichlorophenyl)-pyridine (B1):

A solution of 3-iodo 4-amino pyridine[1] (2.55 g, 11.6 mmole), Pd(PPh$_3$)$_4$ (0.67 g, 0.58 mmole) and aqueous solution of Na$_2$CO$_3$ (17.4 ml, 2M) in toluene (60 ml) is added to a solution of dichlorobenzene boronic acid (4.56 g, 23.2 mmole) in ethanol (17.6 ml). The mixture is heated at reflux for 14 h., diluted with ethyl acetate and washed with saturated NH$_4$Cl solution. The organic layer is dried over sodium sulfate and concentrated in vacuo, The residue is chromatographed on silica gel to give B1.

2-methyl 4-hydroxy-8-(2',4'-dichlorophenyl)1,6-naphthyridine (B2):

A solution of B1 (2.41 g, 10.1 mmole), ethyl acetate (1.31 g, 10.1 mmole) and p-toluenesulfonic acid (70 mg) in benzene (50 ml) is heated at reflux for 2 h. during which 10 ml of solvent is removed by distillation. After evaporation, the residue is added to boiling diphenyl ether (10 ml) and heating is continued for 1 h; then the solution is cooled and

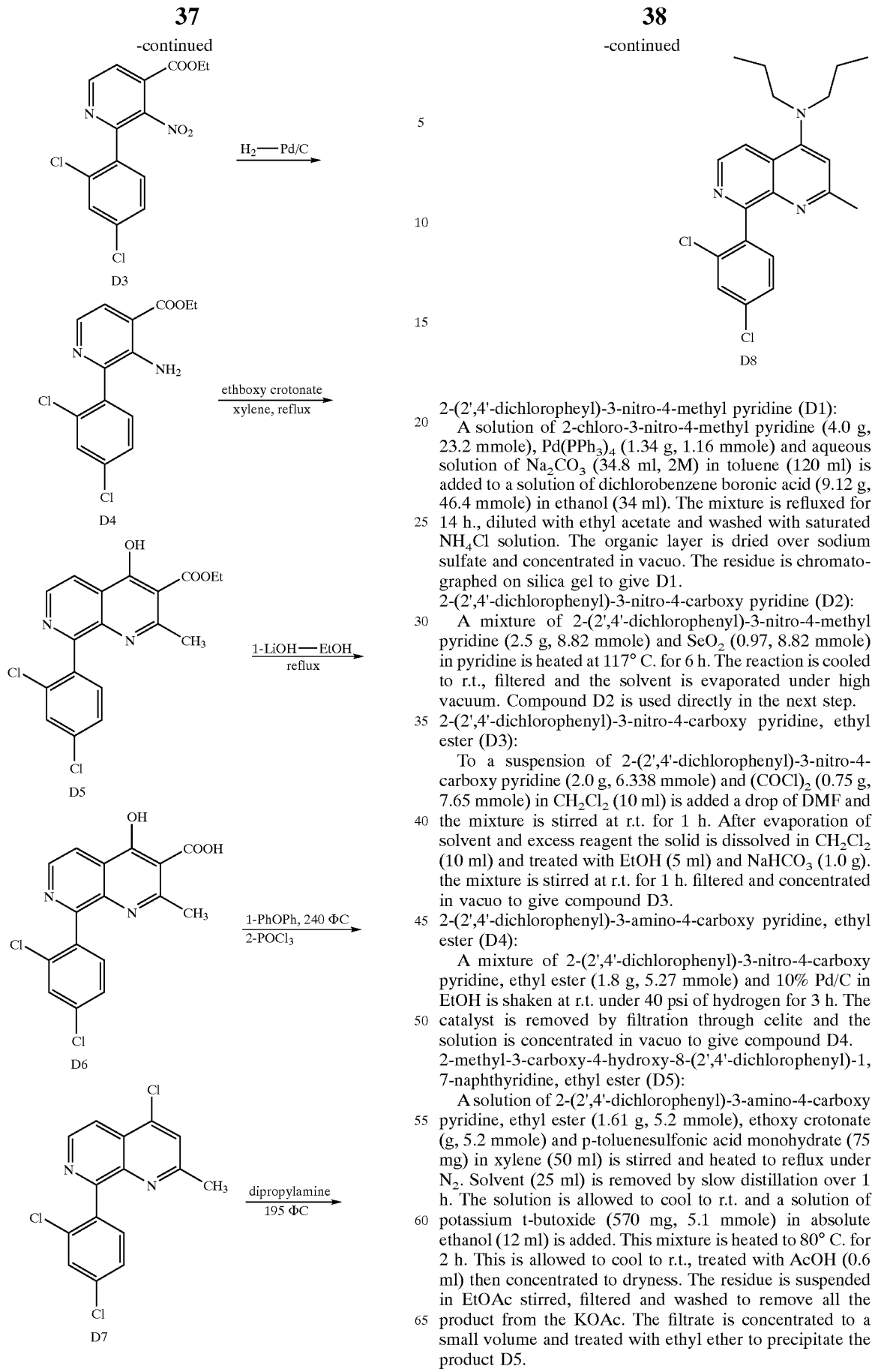

2-(2',4'-dichlorpheyl)-3-nitro-4-methyl pyridine (D1):
A solution of 2-chloro-3-nitro-4-methyl pyridine (4.0 g, 23.2 mmole), Pd(PPh₃)₄ (1.34 g, 1.16 mmole) and aqueous solution of Na₂CO₃ (34.8 ml, 2M) in toluene (120 ml) is added to a solution of dichlorobenzene boronic acid (9.12 g, 46.4 mmole) in ethanol (34 ml). The mixture is refluxed for 14 h., diluted with ethyl acetate and washed with saturated NH₄Cl solution. The organic layer is dried over sodium sulfate and concentrated in vacuo. The residue is chromatographed on silica gel to give D1.

2-(2',4'-dichlorophenyl)-3-nitro-4-carboxy pyridine (D2):
A mixture of 2-(2',4'-dichlorophenyl)-3-nitro-4-methyl pyridine (2.5 g, 8.82 mmole) and SeO₂ (0.97, 8.82 mmole) in pyridine is heated at 117° C. for 6 h. The reaction is cooled to r.t., filtered and the solvent is evaporated under high vacuum. Compound D2 is used directly in the next step.

2-(2',4'-dichlorophenyl)-3-nitro-4-carboxy pyridine, ethyl ester (D3):
To a suspension of 2-(2',4'-dichlorophenyl)-3-nitro-4-carboxy pyridine (2.0 g, 6.338 mmole) and (COCl)₂ (0.75 g, 7.65 mmole) in CH₂Cl₂ (10 ml) is added a drop of DMF and the mixture is stirred at r.t. for 1 h. After evaporation of solvent and excess reagent the solid is dissolved in CH₂Cl₂ (10 ml) and treated with EtOH (5 ml) and NaHCO₃ (1.0 g). the mixture is stirred at r.t. for 1 h. filtered and concentrated in vacuo to give compound D3.

2-(2',4'-dichlorophenyl)-3-amino-4-carboxy pyridine, ethyl ester (D4):
A mixture of 2-(2',4'-dichlorophenyl)-3-nitro-4-carboxy pyridine, ethyl ester (1.8 g, 5.27 mmole) and 10% Pd/C in EtOH is shaken at r.t. under 40 psi of hydrogen for 3 h. The catalyst is removed by filtration through celite and the solution is concentrated in vacuo to give compound D4.

2-methyl-3-carboxy-4-hydroxy-8-(2',4'-dichlorophenyl)-1,7-naphthyridine, ethyl ester (D5):
A solution of 2-(2',4'-dichlorophenyl)-3-amino-4-carboxy pyridine, ethyl ester (1.61 g, 5.2 mmole), ethoxy crotonate (g, 5.2 mmole) and p-toluenesulfonic acid monohydrate (75 mg) in xylene (50 ml) is stirred and heated to reflux under N₂. Solvent (25 ml) is removed by slow distillation over 1 h. The solution is allowed to cool to r.t. and a solution of potassium t-butoxide (570 mg, 5.1 mmole) in absolute ethanol (12 ml) is added. This mixture is heated to 80° C. for 2 h. This is allowed to cool to r.t., treated with AcOH (0.6 ml) then concentrated to dryness. The residue is suspended in EtOAc stirred, filtered and washed to remove all the product from the KOAc. The filtrate is concentrated to a small volume and treated with ethyl ether to precipitate the product D5.

2-methyl-3-carboxy-4-hydroxy-8-(2',4'-dichlorophenyl)-1,7-naphthyridine (D6):

A 2-methyl-3-carboxy-4-hydroxy-8-(2',4'-dichlorophenyl)-1,7-naphthyridine, ethyl ester (1.80 g, 4.8 mmole) and LiOH (17.5 ml, 1M) in ethanol (10 ml) is stirred and heated to reflux under $N_2$ for 16 h. The solution is allowed to cool to r.t. then poured into a mixture of hydrochloric acid (15 ml, 1M) in water (100 ml). This is extracted with EtOAc, the organic phase is washed with brine, dried and concentrated to give the title compound. This is used directly in the next step.

2-methyl-4-chloro-8-(2',4'-dichlorophenyl)-1,7-naphthyridine (D7):

A solution of 2-methyl-3-carboxy-4-hydroxy-8-(2',4'-dichlorophenyl)-1,7-naphthyridine (0.41 g, 1.2 mmole) in diphenyl ether (0.4 ml) is stirred and heated to 230° C. for 1.5 h. The solution is allowed to cool to r.t., and $POCl_3$ (0.8 ml) is added. This mixture is heated to 100° C. for 2 h, then allowed to cool to r.t., and poured into 5% $NaHCO_3$. This is extracted with EtOAc, the organic phase washed with brine, dried and concentrated. The product is purified by flash chromatography on silica gel to give the title compound D7.

2-dimethyl-4-dipropylamino-8-(2',4'-dichlorophenyl)-1,7-naphthyridine (D8):

A mixture of 2-methyl-4-chloro-8-(2',4'-dichlorophenyl)-1,7-naphthyridine (6.47 mg, 0.02 mmole), p-toluenesulfonic acid (20 mg) and dipropylamine (50 µl) is stirred and heated to 195° C. for 1.5 h. The solution is allowed to cool to r.t., then dissolved in a mixture of water and EtOAc. This is extracted with EtOAc, the organic phase washed with brine, dried and concentrated. The product is purified by prep. TLC ($SiO_2$) using ethyl acetate/hexane, to give the product D8.

Example 16

Synthesis of Representative Compounds of Structure (VI)

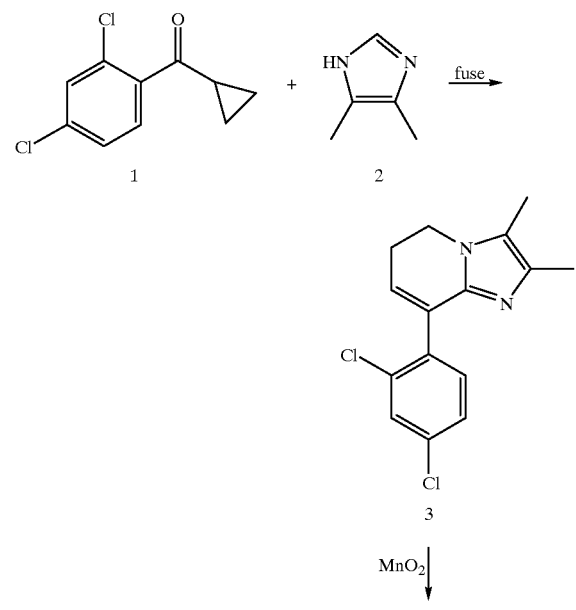

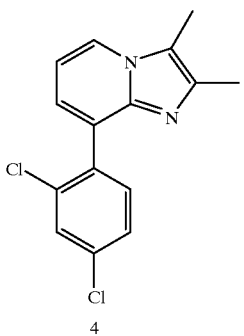

2,3-Dimethyl-8-(2,4-dichlorophenyl)-5,6-dihydroimidazo[1,2-a]pyridine (3)

Cyclopropyl 2,4-dichlorophenyl ketone (1) (54 g, 0.25 mol) and 4,5-dimethylimidazole (2) (90 g, 1 mol) are combined and heated at 200 to 210° C. under nitrogen for 20 hours. The reaction is cooled and diluted with ethyl acetate (700 ml). The ethyl acetate solution is washed with saturated aq potassium carbonate (300 ml) and water (4×200 ml) and dried over sodium sulfate. The drying agent is removed by filtration and the solvent is removed in vacuo to provide 3.

2,3-Dimethyl-8-(2,4-dichlorophenyl)imidazo[1,2-a]pyridine (4)

2,3-Dimethyl-8-(2,4-dichlorophenyl)-5,6-dihydroimidazo[1,2-a]pyridine (3) (29.3 g, 0.1 mol) is dissolved in methylene chloride (1 L) and activated manganese dioxide (120 g) is added. The mixture is heated at reflux for 16 hours with stirring. The catalyst is removed by filtration of the reaction through a Celite pad and the filtrate is evaporated to a solid (4).

Example 17

Representative Compounds Having CRF Receptor Binding Activity

The compounds of this invention may be evaluated for binding activity to the CRF receptor by a standard radioligand binding assay as generally described by DeSouza et al. (J. Neurosci. 7:88–100, 1987). By utilizing various radiolabeled CRF ligands, the assay may be used to evaluate the binding activity of the compounds of the present invention with any CRF receptor subtype. Briefly, the binding assay involves the displacement of a radiolabeled CRF ligand from the CRF receptor.

More specifically, the binding assay is performed in 1.5 ml Eppendorf tubes using approximately $1×10^6$ cells per tube stably transfected with human CRF receptors. Each tube receives about 0.1 ml of assay buffer (e.g, Dulbecco's phosphate buffered saline, 10 mM magnesium chloride, 20 µM bacitracin) with or without unlabeled sauvagine, urotensin I or CRF (final concentration, 1 µM) to determine nonspecific binding, 0.1 ml of [$^{125}$I] tyrosine—ovine CRF (final concentration ~200 pM or approximately the $K_D$ as determined by Scatchard analysis) and 0.1 ml of a membrane suspension of cells containing the CRF receptor. The mixture is incubated for 2 hours at 22° C. followed by the separation of the bound and free radioligand by centrifugation. Following two washes of the pellets, the tubes are cut just above the pellet and monitored in a gamma counter for radioactivity at approximately 80% efficiency. All radioligand binding data may be analyzed using the non-linear least-square curve-fitting program LIGAND of Munson and Rodbard (Anal. Biochem. 107:220, 1990).

Example 18

CRF-Stimulated Adenylate Cyclase Activity

The compounds of the present invention may also be evaluated by various functional testing. For example, the compounds of the present invention may be screened for CRF-stimulated adenylate cyclase activity. An assay for the determination of CRF-stimulated adenylate cyclase activity may be performed as generally described by Battaglia et al. (*Synapse* 1:572, 1987), with modifications to adapt the assay to whole cell preparations.

More specifically, the standard assay mixture may contain the following in a final volume of 0.5 ml: 2 mM L-glutamine, 20 mM HEPES. and 1 mM IMBX in DMEM buffer. In stimulation studies, whole cells with the transfected CRF receptors are plated in 24-well plates and incubated for 1 h at 37° C. with various concentrations of CRF-related and unrelated peptides in order to establish the pharmacological rank-order profile of the particular receptor subtype. Following the incubation, the media is aspirated, the wells rinsed once gently with fresh media, and the media aspirated. To determine the amount of intracellular cAMP, 300 µl of a solution of 95% ethanol and 20 mM aqueous hydrochloric acid is added to each well and the resulting suspensions are incubated at −20° C. for 16 to 18 hours. The solution is removed into 1.5 ml Eppendorf tubes and the wells washed with an additional 200 µl of ethanol/aqueous hydrochloric acid and pooled with the first fraction. The samples are lyophilized and then resuspended with 500 µl sodium acetate buffer. The measurement of cAMP in the samples is performed using a single antibody kit from Biomedical Technologies Inc. (Stoughton, Mass.). For the functional assessment of the compounds, a single concentration of CRF or related peptides causing 80% stimulation of cAMP production is incubated along with various concentrations of competing compounds ($10^{-12}$ to $10^{-6}$ M).

It will be appreciated that, although specific embodiments of the invention have been described herein for purposes of illustration, various modifications may be made without departing from the spirit and scope of the invention. Accordingly, the invention is not limited except as by the appended claims.

What is claimed is:

1. A compound having the following structure:

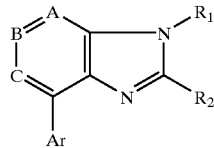

or a stereoisomers or pharmaceutically acceptable salts thereof, wherein:

A, B and C are selected from CR and N, with the proviso that when one of A, B, and C, is N, the other two of A, B, and C are CR;

R is selected from hydrogen and $C_{1-6}$alkyl;

$R_1$ is selected from $NR_3R_4$ and $R_5$;

$R_2$ is $C_{1-6}$alkyl;

$R_3$ is selected from hydrogen, $C_{1-6}$alkyl, mono- or di($C_{3-6}$cycloalkyl)methyl, $C_{3-6}$cycloalkyl; $C_{3-6}$alkenyl; hydroxy$C_{1-6}$alkyl, $C_{1-6}$alkylcarbonyloxy$C_{1-6}$alkyl and $C_{1-6}$alkyloxy$C_{1-6}$alkyl;

$R_4$ and $R_5$ are independently selected from $C_{1-8}$alkyl, mono- or di($C_{3-6}$cycloalkyl)methyl, $Ar^1CH_2$, $C_{3-6}$alkenyl, $C_{1-6}$alkyloxy$C_{1-6}$alkyl, hydroxy$C_{1-6}$alkyl, thienylmethyl, furanylmethyl, $C_{1-6}$alkylthio$C_{1-6}$alkyl, morpholinyl, mono- or di($C_{1-6}$alkyl)amino$C_{1-6}$alkyl, di($C_{1-6}$alkyl)amino, $C_{1-6}$alkylcarbonyl$C_{1-6}$alkyl, $C_{1-6}$alkyl substituted with imidazolyl; or a radical of the formula —($C_{1-6}$alkanediyl)-O—CO—$Ar^1$;

or $R_3$ and $R_4$ taken together with the nitrogen atom to which they are attached form a pyrrolidinyl, piperidinyl, homopiperidinyl or morpholinyl group, optionally substituted with $C_{1-6}$alkyl or $C_{1-6}$alkyloxy;

Ar is selected from phenyl substituted with 1, 2 or 3 substituents independently selected from halo, $C_{1-6}$alkyl, triflouromethyl, cyano, $C_{1-6}$alkyloxy, benzyloxy, $C_{1-6}$alkylthio, nitro, amino and mono- and di($C_{1-6}$alkyl)amino; and pyridinyl substituted with 1, 2 or 3 substituents independently selected from halo, $C_{1-6}$alkyl, triflouromethyl, hydroxy, cyano, $C_{1-6}$alkyloxy, benzyloxy, $C_{1-6}$alkylthio, nitro, amino, mono- and di($C_{1-6}$alkyl)amino and piperidinyl; and $Ar^1$ is selected from phenyl, pyridinyl, and phenyl substituted with 1, 2 or 3 substituents independently selected from halo, $C_{1-6}$alkyl, $C_{1-6}$alkyloxy, di($C_{1-6}$alkyl)amino$C_{1-6}$alkyl, triflouromethyl and $C_{1-6}$alkyl substituted with morpholinyl.

2. A method for treating a disorder selected from the group consisting of depression, anxiety disorder, panic disorder, obsessive-compulsive disorder, abnormal aggression, unstable angina, reactive hypertension, anorexia nervosa, bulimia, irritable bowel syndrome, stress-induced immune suppression, stroke, inflammation, Cushing's disease, infantile spasms, epilepsy, and substance abuse or withdrawal in a warm-blooded animal, comprising administering to the animal an effective amount of a compound of claim 1.

3. The method of claim 2 wherein the disorder is stroke.

4. The method of claim 2 wherein said disorder is anxiety or depression.

5. The method of claim 2 wherein said disorder is irritable bowel syndrome, inflammation, anorexia nervosa, seizures, or substance abuse.

* * * * *